US008097596B2

(12) United States Patent
Dale

(10) Patent No.: US 8,097,596 B2
(45) Date of Patent: Jan. 17, 2012

(54) COMPOSITIONS AND METHODS FOR THE TREATMENT OF MUSCLE WASTING

(75) Inventor: Roderic M. K. Dale, Wilsonville, OR (US)

(73) Assignee: Lakewood-Amedex, Inc., Lakewood Ranch, FL (US)

( * ) Notice: Subject to any disclaimer, the term of this patent is extended or adjusted under 35 U.S.C. 154(b) by 1138 days.

(21) Appl. No.: 11/479,112

(22) Filed: Jun. 30, 2006

(65) Prior Publication Data

US 2008/0119426 A1    May 22, 2008

(51) Int. Cl.
A61K 48/00    (2006.01)
(52) U.S. Cl. .................................... 514/44 R
(58) Field of Classification Search .............. 514/44 R
See application file for complete search history.

(56) References Cited

U.S. PATENT DOCUMENTS

| | | | |
|---|---|---|---|
| 4,987,071 A | 1/1991 | Cech et al. | |
| 5,254,678 A | 10/1993 | Haseloff et al. | |
| 5,603,915 A | 2/1997 | Nelson et al. | |
| 5,830,140 A | 11/1998 | Dillinger et al. | |
| 5,834,192 A | 11/1998 | Akerblom et al. | |
| 5,972,636 A | 10/1999 | Goldberg | |
| 6,326,174 B1 | 12/2001 | Joyce et al. | |
| 6,387,656 B1 | 5/2002 | Jessell et al. | |
| 6,506,559 B1 | 1/2003 | Fire et al. | |
| 6,617,438 B1 | 9/2003 | Beigelman et al. | |
| 6,653,467 B1 | 11/2003 | Matsuo et al. | |
| 6,656,475 B1 | 12/2003 | Lee et al. | |
| 6,727,355 B2 | 4/2004 | Matsuo et al. | |
| 2004/0038303 A1 | 2/2004 | Unger | |
| 2005/0124566 A1 | 6/2005 | Robin et al. | |
| 2006/0003959 A1* | 1/2006 | Burden et al. ................. | 514/44 |

FOREIGN PATENT DOCUMENTS

| | | |
|---|---|---|
| JP | 11-140930 A | 5/1999 |
| WO | WO-95/29241 A2 | 11/1995 |
| WO | WO-95/31551 A1 | 11/1995 |
| WO | WO-95/35032 A1 | 12/1995 |
| WO | WO02/10214 | 2/2002 |
| WO | WO-2004/031350 A2 | 4/2004 |
| WO | WO-2006/086667 A2 | 8/2006 |
| WO | WO-2008/005002 A1 | 1/2008 |
| WO | WO-2008/005019 A1 | 1/2008 |

OTHER PUBLICATIONS

Li, Jun-sheng; The Effect of Chemical Modification on the Biological Activity of Oligonucleotide, Journal of Guangxi University of Technology, 13(2): 6-9 (2002).
Sun, Xue-guang, Progress in the Stability and Biological Function of Triple Helix Nucleic Acid; Prog. Biochem. Biophys. 25(4), 318-324 (1998).
Wu, Fei et al., Progress of Chemical Modifications of Antisense Oligonucleotides, Chinese Journal of Pharmaceuticals, 34(9):469-475 (2003).
Acharyya, et al., "Cancer Cachexia is Regulated by Selective Targeting of Skeletal Muscle Gene Products" *J. Clin. Invest.*, 114(3):370-378 (2004).
Altschul, et al., "Gapped BLAST and PSI-BLAST: A New Generation of Protein Databse Search Programs" *Nucleic Acids Res.*, 25(17):3389-3402 (1997).
Elbashir, et al., "Duplexes of 21-Nucleotide RNAs Mediate RNA Interference in Cultured Mammalian Cells" *Nature*, 411(6836):494-498 (2001).
Forster, et al, "Self-Cleavage of Plus and Minus RNAs of a Virusoid and a Structural Model for the Active Sites" *Cell*, 49:211-220 (1987).
GenBank Accession No. AB021709, Aug. 5, 1999.
GenBank Accession No. AB033541, Jan. 27, 2009.
GenBank Accession No. AF019621, Nov. 21, 1997.
GenBank Accession No. AF019622, Nov. 21, 1997.
GenBank Accession No. AF027964, Dec. 17, 1997.
GenBank Accession No. AF033855, Mar. 26, 1998.
GenBank Accession No. AF059516, Sep. 29, 1999.
GenBank Accession No. AF073526, Oct. 8, 1999.
GenBank Accession No. AF104922, Dec. 17, 1998.
GenBank Accession No. AF294790, Sep. 8, 2000.
GenBank Accession No. AF346599, Dec. 22, 2004.
GenBank Accession No. AF441120, Dec. 20, 2001.
GenBank Accession No. AY061884, Nov. 18, 2004.
GenBank Accession No. AY169410, Jun. 27, 2003.
GenBank Accession No. AY367768, Nov. 15, 2003.
GenBank Accession No. AY436347, Nov. 9, 2003.
GenBank Accession No. AY590150, Apr. 28, 2004.
GenBank Accession No. AY825248, Dec. 7, 2004.
GenBank Accession No. BC006656, Dec. 2, 2006.
GenBank Accession No. BC008152, Jul. 15, 2006.
GenBank Accession No. L19067, Aug. 23, 1994.
GenBank Accession No. M61909, Mar. 11, 1994.
GenBank Accession No. M62399, Apr. 27, 1993.
GenBank Accession No. M83667, Jan. 7, 1995.
GenBank Accession No. NM_000565, Dec. 20, 2009.
GenBank Accession No. NM_000576, Jan. 3, 2010.
GenBank Accession No. NM_000594, Jan. 3, 2010.
GenBank Accession No. NM_000600, Jan. 3, 2010.
GenBank Accession No. NM_001001525, Dec. 6, 2009.
GenBank Accession No. NM_001065, Dec. 27, 2009.
GenBank Accession No. NM_001106, Jun. 26, 2009.
GenBank Accession No. NM_001455, Dec. 20, 2009.
GenBank Accession No. NM_002015, Dec. 27, 2009.
GenBank Accession No. NM_002165, Jan. 3, 2010.
GenBank Accession No. NM_002478, Jan. 3, 2010.
GenBank Accession No. NM_003183, Jan. 3, 2010.
GenBank Accession No. NM_003998, Jan. 3, 2010.
GenBank Accession No. NM_004346, Dec. 27, 2009.
GenBank Accession No. NM_004530, Jan. 3, 2010.
GenBank Accession No. NM_005178, Dec. 7, 2009.
GenBank Accession No. NM_007397, Dec. 7, 2009.
GenBank Accession No. NM_008361, Jan. 3, 2010.
GenBank Accession No. NM_008610, Dec. 20, 2009.

(Continued)

*Primary Examiner* — J. E. Angell
(74) *Attorney, Agent, or Firm* — Mintz Levin Cohn Ferris Glovsky and Popeo, P.C.; Ingrid A. Beattie

(57) ABSTRACT

The invention provides compositions of oligonucleotides targeted at genes involved in muscle wasting and/or muscle growth. In some embodiments, the oligonucleotides are modified. In some embodiments, the compositions contain one, or more than one, oligonucleotide. The invention also provides methods and kits using the compositions of the invention for the treatment of muscle wasting conditions and/or the promotion of muscle growth.

13 Claims, 5 Drawing Sheets

OTHER PUBLICATIONS

GenBank Accession No. NM_009810, Jan. 3, 2010.
GenBank Accession No. NM_010754, Jan. 3, 2010.
GenBank Accession No. NM_010834, Dec. 7, 2009.
GenBank Accession No. NM_010866, Dec. 27, 2009.
GenBank Accession No. NM_011609, Dec. 27, 2009.
GenBank Accession No. NM_013693, Jan. 3, 2010.
GenBank Accession No. NM_019739, Dec. 20, 2009.
GenBank Accession No. NM_019740, Dec. 13, 2009.
GenBank Accession No. NM_031168, Jan. 3, 2010.
GenBank Accession No. NM_033292, Dec. 7, 2009.
GenBank Accession No. NM_058229, Jun. 28, 2009.
GenBank Accession No. NM_146078, Oct. 4, 2009.
GenBank Accession No. NM_148177, Jun. 28, 2009.
GenBank Accession No. NM_181359, Dec. 20, 2009.
GenBank Accession No. NM_201559, Dec. 20, 2009.
GenBank Accession No. NM_214435, Nov. 22, 2009.
GenBank Accession No. X53802, Apr. 18, 2005.
Grobet, et al., "Modulating Skeletal Muscle Mass by Postnatal, Muscle-Specific Inactivation of the Myostatin Gene" *Genesis*, 35(4):227-238 (2003).
Guerrier-Takada, et al., "The RNA Moiety of Ribonuclease P is the Catalytic Subunit of the Enzyme" *Cell*, 35:849-857 (1983).
Hampel, et al., "Hairpin' Catalytic RNA Model: Evidence for Helices and Sequence Requirement for Substrate RNA" *Nucleic Acids Res.*, 18(2):299-304 (1990).
Haseloff, et al., "Simple RNA Enzymes With New and Highly Specific Endoribonuclease Activities" *Nature*, 334:585-591 (1988).
Heindenreich, et al., "Chemically Modified RNA: Approaches and Applications" *J. FASEB*, 70(1):90-96 (1993).
Karlin, et al., "Methods for Assessing the Statistical Significance of Molecular Sequence Features by Using General Scoring Schemes" *Proc. Natl. Acad. Sci.*, 87:2264-2268 (1990).
Mathews, et al., "Expanded Sequence Dependence of Thermodynamic Parameters Improves Prediction of RNA Secondary Structure" *J. Mol. Biol.*, 288:911-940 (1999).
Mathews, et al., "Predicting Oligonucleotide Affinity to Nucleic Acid Targets" *RNA*, 5:1458-1469 (1999).
McPherron, et al., "Regulation of Skeletal Muscle Mass in Mice by a New TGF-β Superfamily Member" *Nature*, 387(6628):83-90 (1997).
Perrotta, et al., "Cleavage of Oligoribonucleotides by a Ribozyme Derived from the Hepatitis δ Virus RNA Sequence" *Biochem.*, 31:16-21 (1992).
Rossi, et al., "The Potential Use of Catalytic RNAs in Therapy of HIV Infection and Other Diseases" *Pharmac. Ther.*, 50:245-254 (1991).
Ruffner, et al., "Sequence Requirements of the Hammerhead RNA Self-Cleavage Reaction" *Biochemistry*, 29:10695-10702 (1990).
Sproat, "Chemical Nucleic Acid Synthesis, Modification and Labelling" *Curr. Opin. Biotechnol.*, 4(1):20-28 (1993).
Sun, et al., "Catalytic Nucleic Acids: From Lab to Applications" *Pharmacol. Rev.*, 52(3):325-347 (2000).
Tuschl, et al., "Targeted mRNA Degradation by Double-Stranded RNA in Vitro" *Genes and Dev.*, 13:3191-3197 (1999).
Walbot, et al., "Plant Development and Ribozymes for Pathogens" *Nature*, 334:196-197 (1988).
Whittemore et al., "Inhibition of Myostatin in Adult Mice Increase Skeletal Muscle Mass and Strength", *Biochem. Biophys. Res. Commun.*, 300(4):965-971 (2003).
Zamore, et al., "RNAi: Double-Stranded RNA Directs the ATP-Dependent Cleavage of mRNA at 21 to 23 Nucleotide Intervals" *Cell*, 101:25-33 (2000).
Lynch, G. S. Emerging drugs for sarcopenia: age-related muscle wasting. Expert Opin Emerg Drugs. 2004; 9(2):345-361.
Sato, et al. Gene silencing of myostatin in differentiation of chicken embryonic myoblasts by small interfering RNA. Am. J. Physiol. Cell Physiol. 2006; 291:C538-545.

* cited by examiner

A

B

C

D

US 8,097,596 B2

COMPOSITIONS AND METHODS FOR THE TREATMENT OF MUSCLE WASTING

BACKGROUND

Increase in muscle growth has been an important field both for treatment of muscle wasting conditions and for farm and food animals. The muscle wasting conditions include Duchenne muscular dystrophy (DMD), multiple types of limb girdle MD (LGMD) and other congenital MDs (CMD), sarcopenia, cancer cachexia, Diabetes mellitus. Progressive muscle damage and muscle loss, tissue inflammation and replacement of healthy muscle with fibrous and fatty tissues result in disability and fatality.

In animal husbandry, such as for food animals, any methods that increase the proportion and weight of muscle will greatly benefit the industry. However, there have been no effective means to treat muscle wasting conditions and to promote muscle growth in animals.

SUMMARY OF INVENTION

In one aspect, the invention provides compositions and methods for treatment of muscle wasting conditions and/or promotion of muscle growth using compositions containing one or more oligonucleotides. In some embodiments the invention provides compositions suitable for administration to an animal containing a modified oligonucleotide containing 7 to 75 contiguous ribose groups linked by achiral 5' to 3' internucleoside phosphate linkages, where the modified oligonucleotide is complementary to a region of a gene selected from the group consisting of the 5' UTR region, translational start site, the 3' UTR, and translational termination site, and wherein the gene is related to a muscle wasting condition. In some embodiments, the modified oligonucleotide has a $T_m$ of about 75-115° C. at a concentration of 1 mM and a length of 10 to 26 bases, or a $T_m$ of about 40° C. to 85° C. at a concentration of 1 pM and a length of 10 to 26 bases. In some embodiments, the oligonucleotide comprises a nucleotide selected from the group consisting of ribonucleotides and deoxyribonucleotides. In some embodiments, the oligonucleotide contains one or more nucleotides in which the 2' position comprises a substituent, for example, hydrogen, methoxy, propoxy, methoxy-ethoxy, fluorine, chlorine, bromine and iodine. In some embodiments, the modified oligonucleotide is 3' and/or 5' end-modified. In some embodiments, the modified oligonucleotide is 3' and/or 5' end-blocked. In some embodiments, the oligonucleotide is an antisense oligonucleotide, e.g., an antisense oligonucleotide complementary to a myostatin gene, for example, an animal, mammalian, or human myostatin gene. In some embodiments, the oligonucleotide comprises a sequence selected from the group consisting of SEQ ID NOS 1-191. In some embodiments, the oligonucleotide comprises an RNAi, ribozyme or deoxyribozyme. In some embodiments, the composition contains a plurality of modified oligonucleotides, e.g., two modified oligonucleotides.

In some embodiments, the invention provides a method of treating a muscle wasting condition comprising administering to an individual suffering from a muscle wasting condition an effective amount a composition of the invention. In some embodiments, the invention provides a method of promoting muscle growth in an individual comprising administering to the individual an effective amount of a composition of the invention. In some embodiments, the individual is a mammal. In some embodiments, the individual is a human.

In some embodiments, the oligonucleotide comprises 7 to 75 modified nucleotides containing contiguous ribose groups linked by achiral 5' to 3' internucleoside phosphate linkages, wherein the modified oligonucleotide is complementary to a region of genes involved in muscle wasting conditions. In some embodiments, the composition contains two, three, four, five, or more than five different modified oligonucleotides. In some embodiments, the modified oligonucleotide is complementary to a region of the gene selected from the group consisting of the 5' UTR region, translational start site, the 3' UTR, and translational termination site. In some embodiments, the modified oligonucleotide has a $T_m$ of about 75-115° C. at a concentration of 1 mM and a length of 10 to 26 bases, or a $T_m$ of about 40° C. to 85° C. at a concentration of 1 pM and a length of 10 to 26 bases. The preferred compositions contain either antisense oligonucleotides or siRNA. The invention provides compositions and methods for treatment of muscle wasting conditions for human and animals. The invention also provides methods for use of compositions in food dietary supplement. The present invention provides compositions and methods for the modulation of expression of genes that code for gene products that are involved in muscle wasting and/or muscle growth conditions.

In one aspect, the invention provides compositions. In some embodiments, the invention provides a composition suitable for administration to an animal comprising a modified oligonucleotide containing contiguous ribose groups linked by achiral 5' to 3' internucleoside phosphate linkages, wherein the modified oligonucleotide is complementary to a region of a gene coding for myostatin or a myostatin receptor. In some embodiments, the composition contains two, three, four, five, or more than five different modified oligonucleotides. In some embodiments, the oligonucleotide comprises about seven to seventy-five nucleotides containing seven or more contiguous ribose groups linked by achiral 5' to 3' internucleoside phosphate linkages. In some embodiments, the modified oligonucleotide is complementary to a region of the gene selected from the group consisting of the 5' UTR region, translational start site, the 3' UTR, and translational termination site. In some embodiments, the modified oligonucleotide has a $T_m$ of about 75-115° C. at a concentration of 1 mM and a length of 10 to 26 bases, or a $T_m$ of about 40° C. to 85° C. at a concentration of 1 pM and a length of 10 to 26 bases. In some embodiments, the ribose group of the oligonucleotide has a modified 2' substituent; in some embodiments the modified substituent is selected from the group consisting of hydrogen, methoxy, propoxy, methoxy-ethoxy, fluorine, chlorine, bromine and iodine. In some embodiments, the modified oligonucleotide is 3' end-blocked. In some embodiments, the modified oligonucleotide is 5' end-blocked.

The invention also provides a pharmaceutical composition comprising a composition suitable for administration to an animal comprising a modified oligonucleotide containing contiguous ribose groups linked by achiral 5' to 3' internucleoside phosphate linkages, wherein the modified oligonucleotide is complementary to a region of a gene coding for myostatin or a myostatin receptor, and a pharmaceutically acceptable excipient.

In some embodiments, the invention provides an antisense oligonucleotide that inhibits the expression of myostatin or myostatin receptor genes, wherein the oligonucleotide is selected from the group consisting of SEQ ID NOS: 1-191.

In other embodiments, the invention provides a composition comprising an interfering RNA (RNAi) that modulates expression of myostatin or a myostatin receptor. In some embodiments, the RNAi composition comprises double-stranded RNA of 21-25 nucleotides with overhangs of 2 nucleotides at both 3' ends. 30-52% of the G+C content of the double stranded region, A/U base-pairing in positions 15-19 in sense strand, and no internal repeats.

In yet other embodiments, the invention provides a composition comprising a DNAzyme, wherein the DNAzyme modulates expression of myostatin or a myostatin receptor. In some embodiments, the DNAzyme comprises a catalytic domain that comprises the nucleotide sequence GGCTAGCTACAACGA (SEQ ID NO: 192) and specifically cleaves mRNA coding for myostatin or a myostatin receptor at any purine:pyrimidine site to which the catalytic domain is directed, a first binding domain contiguous with the 5'end of the catalytic domain, and a second binding domain contiguous with the 3'end of the catalytic domain, wherein each binding domain hybridizes with a region immediately flanking the cleavage site.

In still other embodiments, the invention provides a composition for the modulation of expression of myostatin or myostatin receptors comprising two or more gene-modulating oligonucleotides, wherein at least one oligonucleotide is targeted to myostatin, and at least one oligonucleotide is targeted to a gene that is not myostatin. In some embodiments the composition contains gene-modulating oligonucleotides that comprise one or more oligonucleotides selected from the group consisting of antisense oligonucleotides, RNAi, and DNAzymes. In some embodiments the composition contains antisense oligonucleotides. In some embodiments the non-myostatin gene is a gene coding for a protein selected from the group consisting of Activin A Receptor IIB, Tolloid metalloproteinase, NF-kappaB, TNF-alpha, MuRF1, Caspase-3, Atrogin-1, RAS, P38 MAPK, MKK 3, MKK 6, JNK, c-myc, c-jun, ASK-1, TAK-1, smad, cyclin dependent kinase inhibitor p21, Gadd45, IL-6, and PIF (Table 1 and Table 2). In some embodiments the composition contains one or more antisense oligonucleotides targeted to myostatin is selected from the oligonucleotides shown in Tables 3, 4, and 5 and one or more antisense oligonucleotides targeted to a non-myostatin gene is selected from the oligonucleotides shown in Table 3 and Table 4.

In another aspect, the invention provides methods. In one embodiment, the invention provides a method of modulating expression of myostatin in a cell containing a myostatin-encoding polynucleotide comprising contacting the cell with an oligonucleotide that modulates the expression of said myostatin-encoding polynucleotide, wherein the oligonucleotide is an antisense oligonucleotide comprising contiguous ribose groups linked by achiral 5' to 3' internucleoside phosphate linkages.

In other embodiments, the invention provides a method of modulating expression of myostatin in a cell containing a myostatin-encoding polynucleotide comprising contacting the cell with an oligonucleotide that modulates the expression of said myostatin-encoding polynucleotide, wherein the oligonucleotide is selected from the group consisting of RNAi, ribozymes, and DNAzymes.

In other embodiments, the invention provides a method of modulating expression of myostatin in a cell containing a myostatin-encoding polynucleotide and a non-myostatin-encoding polynucleotide comprising contacting the cell with a first gene-modulating oligonucleotide and a second gene-modulating oligonucleotide, wherein the first oligonucleotide modulates the expression of said myostatin-encoding polynucleotide and the second oligonucleotide modulates the expression of a polynucleotide selected from the group consisting of said myostatin-encoding polynucleotide and said non-myostatin-encoding polynucleotide. In some of these embodiments, the oligonucleotides are selected from the group consisting of antisense oligonucleotides, RNAi, ribozymes, and DNAzymes. In some embodiments, the oligonucleotides comprise a first antisense oligonucleotide and a second antisense oligonucleotide In another embodiment, the invention provides a method of modulating expression of myostatin in an animal comprising administering to the animal an oligonucleotide that modulates the expression of a myostatin-encoding polynucleotide, wherein the oligonucleotide is administered at a dose of 0.01 to 100 mg/kg. In some of these embodiments, the animal is a food animal and the administration results in increased muscle mass.

In another embodiment, the invention provides a method of modulating expression of myostatin in an animal comprising administering to the animal an oligonucleotide that modulates the expression of a myostatin-encoding polynucleotide, wherein the oligonucleotide is an antisense oligonucleotide comprising contiguous ribose groups linked by achiral 5' to 3' internucleoside phosphate linkages. In some of these embodiments, the animal is a food animal and the administration results in increased muscle mass.

In yet another embodiment, the invention provides a method of modulating expression of myostatin in an animal comprising administering to the animal an oligonucleotide that modulates the expression of a myostatin-encoding polynucleotide, wherein the oligonucleotide is selected from the group consisting of RNAi, ribozymes, and DNAzymes. In some of these embodiments, the animal is a food animal and the administration results in increased muscle mass.

In still yet another embodiment, the invention provides a method of modulating expression of myostatin in an animal comprising administering to the animal a first gene-modulating oligonucleotide and a second gene-modulating oligonucleotide, wherein the first oligonucleotide modulates the expression of a myostatin-encoding polynucleotide and the second oligonucleotide modulates the expression of a polynucleotide selected from the group consisting of a myostatin-encoding polynucleotide and a non-myostatin-encoding polynucleotide. In some of these embodiments, the animal is a food animal and the administration results in increased muscle mass.

In another embodiment, the invention provides a method of treating an animal suffering from a muscle-wasting condition comprising administering to the animal an oligonucleotide that modulates the expression of a myostatin-encoding polynucleotide, wherein the oligonucleotide is administered at a dose of 0.001 to 100 mg/kg.

In another embodiment, the invention provides a method of treating an animal suffering from a muscle-wasting condition comprising administering to the animal an oligonucleotide that modulates the expression of a myostatin-encoding polynucleotide, wherein the oligonucleotide is an antisense oligonucleotide comprising contiguous ribose groups linked by achiral 5' to 3' internucleoside phosphate linkages.

In still another embodiment, the invention provides a method of treating an animal suffering from a muscle-wasting condition comprising administering to the animal an oligonucleotide that modulates the expression of a myostatin-encoding polynucleotide, wherein the oligonucleotide is selected from the group consisting of RNAi, ribozymes, and DNAzymes The invention also provides a method of treating an animal suffering from a muscle-wasting condition comprising administering to the animal a first gene-modulating oligonucleotide and a second gene-modulating oligonucleotide, wherein the first oligonucleotide modulates the expression of a myostatin-encoding polynucleotide and the second oligonucleotide modulates the expression of a polynucleotide selected from the group consisting of a myostatin-encoding polynucleotide and a non-myostatin-encoding polynucleotide. In some embodiments, the oligonucleotides are selected from the group consisting of antisense oligonucleotides, RNAi, ribozymes, and DNAzymes.

In a further aspect, the invention provides kits that contain one or more of the compositions of the invention and, optionally, instructions for the use of the compositions.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
FIG. 1 is a bar graph representing muscle weight in three groups of mice treated with saline, mock, or RNA antisense oligonucleotides.

The present invention provides compositions and methods for the modulation of expression of genes that code for gene products that are involved in muscle wasting and/or muscle growth conditions. Accordingly, the invention provides compositions and methods using the compositions, for enhancement of muscle growth and treatment of diseases associated with inadequate muscle growth, abnormal fat accumulation, or muscle wasting. The invention also provides compositions and methods using the compositions, for enhancing normal muscle growth where such enhancement is desired (e.g., in farm animals).

Generally, the compositions and methods of the invention utilize oligonucleotides that modulate gene expression, also referred to herein as "gene modulators" and "gene-modulating oligonucleotides." Exemplary gene modulators of the invention include antisense oligonucleotides, interfering RNA (RNAi), ribozymes, and DNAzymes. In some embodiments, the invention provides a single gene modulator targeted at a single gene involved in muscle growth and maintenance, e.g., myostatin. In other embodiments, the invention provides combinations of gene modulators. These combinations include: combinations of different types of gene modulators, combinations of gene modulators targeted to different parts of the same gene, and combinations of gene modulators targeted to different genes, as well as combinations of any of the aforementioned combinations.

The invention further provides modified oligonucleotides for use in any of the above compositions. In some preferred embodiments, oligonucleotides used in the invention can be, e.g., end-blocked, protonated, exhibit substantial acid resistance, substantial nuclease resistance, and/or contain achiral internucleoside phosphate linkages and modified ribose or deoxyribose substituents.

The invention further provides methods using the compositions of the invention. Methods include methods of treating animals (e.g. mammals, humans) by modulating gene expression in cells by contacting cells with compositions of the invention. Methods also include methods of treatment of disorders using the gene modulating compositions of the invention. Disorders for treatment include muscle wasting disorders or disorders associated with decreased muscle mass and/or increased obesity. As used herein, the term "muscle wasting disorder," used synonymously herein with the term "muscle wasting condition," encompasses disorders or conditions in which muscle wasting is one of the primary symptoms, such as muscular dystrophy, spinal cord injury, neurodegenerative diseases, anorexia, sarcopenia, cachexia, muscular atrophy due to immobilization, prolonged bed rest, or weightlessness, and the like, as well as disorders in which an abnormally high fat-to-muscle ratio is implicated in a disease or pre-disease state, e.g., Type II diabetes or Syndrome X. In addition, the invention provides methods of increasing muscle mass in animals where such an increase is desirable, e.g., in food animals such as mammals and fish.

In addition, the invention provides kits that provide compositions of the invention, optionally including instructions for use of the compositions in methods of the invention.

The gene modulators of the invention include antisense oligonucleotides, interfering RNA (RNAi), ribozymes, and DNAzymes. Compositions of the invention contain one or more gene modulators that is/are targeted to one or more areas of one or more genes. A composition containing a nucleic acid "modulates" or is "capable of modulating" or is a "modulator" of gene expression if the nucleic acid modulates gene expression or if the nucleic acid encodes a gene product that modulates gene expression. As used herein, the term "modulate" includes both inhibition and stimulation, as well as other changes (e.g., production of a modified gene product) in gene expression. The term "inhibition" is intended to include both complete and partial inhibition of expression. In various embodiments, gene expression is inhibited to a level of about 1-99%, or at least about 1%, 5%, 10%, 20%, 30%, 40%, 50%, 60%, 70%, 80%, 90%, 95%, 98%, or 99% lower than the wild type level of gene expression. In some embodiments, expression is inhibited to a level at least about 1-99%, or at least about 1%, 5%, 10%, 20%, 30%, 40%, 50%, 60%, 70%, 80%, 90%, 95%, 98%, or 99% lower than the wild type level of gene expression.

Genes may be chosen for modulation based on their involvement in one or more pathways that are altered in the disorder to be treated. In some embodiments, the invention provides compositions that contain a gene modulator targeted to one area of one gene, e.g.; myostatin. In some embodiments, the invention provides gene modulators that are targeted to more than one area of one gene, e.g., myostatin. In some embodiments, the invention provides gene modulators that are targeted to multiple genes, e.g., myostatin and myostatin receptor genes, as well as other genes described herein (Table 1 and Table 2). In these embodiments, more than one area of a gene may be targeted I. Compositions of the Invention The compositions of the invention include one or more agents capable of modulating expression of a gene or genes associated with muscle wasting and/or muscle growth, and the conditions associated with them. Typically, the gene modulators of the invention are inhibitory to gene expression and include, without limitation, antisense oligonucleotides, interfering RNA (RNAi), ribozymes, and DNAzymes. Compositions of the invention contain one or more gene modulators that is/are targeted to one or more areas of one or more genes. In some embodiments, the invention provides compositions that contain a gene modulator targeted to one area of one gene, e.g., myostatin. In some embodiments, the invention provides gene modulators that are targeted to more than one area of one gene, e.g., myostatin. In some embodiments, the invention provides gene modulators that are targeted to multiple genes, e.g., myostatin, myostatin receptor genes, and/or myostatin transcription factors. In these embodiments, more than one area of a gene may be targeted.

In preferred embodiments, the invention provides compositions that contain combinations of gene modulators for enhancement of muscle growth and treatment of diseases associated with inadequate muscle growth or muscle wasting, or for enhancing normal muscle growth (e.g., in farm animals). These combinations include: combinations of different types of gene modulators, combinations of gene modulators targeted to different parts of the same gene, and combinations of gene modulators targeted to different genes, as well as combinations of any of the aforementioned combinations.

The invention further provides modified oligonucleotides for use in any of the above combinations. In embodiments, oligonucleotides used in the invention can be, e.g., end-blocked, protonated, exhibit substantial acid resistance, substantial nuclease resistance, and/or contain achiral internucleoside phosphate linkages and modified ribose or deoxyribose substituents.

The compositions and methods of the invention may be applied to any gene for which it is desired to alter expression in order to provide a therapeutic effect in muscle wasting disorders, or to produce a desired increase in muscle mass. In general, the major targets are genes involved in muscle growth and maintenance; however, in the majority of cases, several pathways involving multiple genes are affected by a given disorder, and the invention provides not only compositions and methods targeted to single genes (e.g., myostatin) but also compositions and methods targeted to multiple genes, or to multiple areas on a single gene, or both.

A. Expression-modulating Compositions

Any type of nucleic acid-based therapeutics that modulates expression of a gene may be used in the compositions and methods of the invention. These include antisense oligonucleotides, ribozymes, interfering RNA (RNAi), and DNAzymes. Each of these approaches has one central theme in common, that is, the recognition of their target DNA or mRNA sequences via Watson-Crick base-pairing. The present invention thus relates to polynucleotides that hybridize to any of the gene sequences described herein, preferably under stringent conditions. A stringent condition refers to a condition that allows nucleic acid duplexes to be distinguished based on their degree of mismatch. Such polynucleotides (e.g., antisense and RNAi) can be used to inhibit the expression of muscle wasting-associated gene product. Such polynucleotides can also serve as probes and primers for research and diagnostic purposes.

The term "oligonucleotides" as used herein, refers to a molecule comprising nucleotides (i.e., ribonucleotides, deoxyribonucleotides, or both). The term includes monomers and polymers of ribonucleotides and deoxyribonucleotides, or mixtures thereof, with the nucleotides being connected together via, for example 5' to 3' linkages, 5' to 2' linkages, etc. The nucleotides used in the oligonucleotides may be naturally occurring or may be synthetically produced analogues that are capable of forming base-pair relationships with naturally occurring base pairs. Examples of non-naturally occurring bases that are capable of forming base-pairing relationships include, but are not limited to, aza and deaza pyrimidine analogues, aza and deaza purine analogues, and other heterocyclic base analogues, wherein one or more of the carbon and nitrogen atoms of the purine and pyrimidine rings have been substituted by heteroatoms, e.g., oxygen, sulfur, selenium, phosphorus, etc.

1. Antisense Oligonucleotides

Antisense oligonucleotides contain short, chemically synthesized DNA or RNA oligonucleotides with base-pair homology against the mRNA target of interest. Without wishing to be limited by theory, it is generally believed that antisense oligonucleotides act to inhibit gene expression by blocking translation of mRNA or by targeting the RNA for degradation by RNase H. Antisense oligonucleotides can block splicing, translation, or nuclear-cytoplasmic transport. The mechanisms of action of antisense oligonucleotides vary depending on the backbone of the oligonucleotide. Antisense oligonucleotides can be complementary to an entire coding region or only to a portion thereof.

An antisense oligonucleotide herein can be, for example, about 5, 10, 15, 20, 25, 30, 35, 40, 45, 50, 60, 70, 80, 90, 100, or more than 100 nucleotides in length. Preferably, the oligonucleotide is about five to about 75 nucleotides in length. The oligonucleotide can also be about eight to about 40, or at about 10 to about 30, or about 15 to about 30 sequential nucleotides. In one embodiment, the oligonucleotide is about 12 to about 26 nucleotides in length.

Typically, the procedure for making an antisense oligonucleotide composition includes: (i) selecting an oligonucleotide that is adjacent to or overlaps a target region of a gene, (ii) determining the Gibbs Free energy value associated with the oligonucleotide in reference to the target gene, (iii) assessing $T_m$ in reference to the target gene, and (iv) performing a sequence database search to determine the oligonucleotide overlaps the 5' UTR, the translational start sequence, the 3' UTR, or the translational termination site of an mRNA of a gene different from the target gene. Accordingly, in some embodiments, the antisense oligonucleotides of the present invention can be directed to a translational start site, a 5' UTR, a 3' UTR, or a termination site. Preferably, the oligonucleotide is adjacent to or overlaps the translational start site of the gene by at least about one base. Still preferred, the oligonucleotide overlaps the translational start site by at least about two bases. Still more preferred, the oligonucleotide overlaps the translational start site by at least about three bases.

It is generally preferable to design an RNA or DNA that has the same or similar base sequence as the portion of the complement of a gene that encodes the 5' end of an RNA. However, a nucleic acid may also have, for example, a same or similar base sequence as other regions of the gene, such as the region encoding a translation start site or the 3' untranslated region. In another example, a nucleic acid may be designed to reflect the region around a splice donor or splice acceptor site, either with or without the intervening intron. Of particular interest are nucleic acid molecules whose sequences comprise all or a fragment of the sequence of the complement of a gene that is over-expressed in individuals exhibiting the disease or condition. The identification of overexpression of a gene can be through molecular means, e.g., detection of expression in affected tissue using conventional molecular techniques (e.g., Sambrook et al. (1989) Molecular Cloning: A Laboratory Manual, Cold Spring Harbor Laboratory Press). Overexpression of a gene may also be detected using array technology, or inferred from the results of protein assays, such as ELISA.

Suitable antisense oligonucleotides for the present invention can be determined by evaluating the Delta G or Gibbs Free energy of oligonucleotide binding to the complementary RNA strand at 37° C. and the $T_m$. The Gibbs Free energy and $T_m$ are measured from the part of the target gene that corresponds to the RNA oligonucleotide that is added. These values can be calculated using, e.g., the program found on ftp://rna.chem.rochester.edu and are described in Matthews et al. (1999) J. Mol. Biol. 288, 911-940 and Matthews et al. (1999) RNA 5, 1458-1469.

Accordingly, some preferred embodiments of the invention provides a composition comprising an oligonucleotide, (i) wherein said oligonucleotide is about 10 to about 30 nucleotides in length, (ii) the Gibbs Free energy of the binding of said oligonucleotide/RNA target duplex at 37° C. is −15 kCal, (iii) said oligonucleotide is complementary to a region within the target gene selected from the group consisting of 5' UTR, translational start site and translational termination site.

The Gibbs free energy is measured between that part of the target gene that corresponds to the oligonucleotide, that part typically being the 5'UTR, translational start site or the translational termination site. In a preferred embodiment, the Gibbs Free energy of the binding of said oligonucleotide/RNA target duplex at 37° C. is $\leq$−20 kCal. Also preferred, the Gibbs Free energy is $\leq$−25 kCal. For 12-14 mer oligonucleotides, the Gibbs Free energy is preferably $\leq$−15 kCal, for 15-17 mer oligonucleotides, the Gibbs Free energy is preferably $\leq$−20 kCal, for 18-20 mer oligonucleotides, the Gibbs Free energy is preferably $\leq$−25 kCal, for 21-23 mer oligonucleotides, the Gibbs Free energy is $\leq$−30 kCal, and for 24-26 mer oligonucleotides, the Gibbs Free energy is $\leq$35 kCal.

Further provided by the present invention is a composition comprising an oligonucleotide, (i) wherein said oligonucleotide is about 10 to about 30 nucleotides in length, (ii) the $T_m$ of said oligonucleotide to a target gene is about 65-90° C., (iii) said oligonucleotide is complementary to a region within the target gene selected from the group consisting of 5' UTR, translational start site an termination site. Preferably, the oligonucleotide has a $T_m$ of about 75-90° C. Still preferred, the oligonucleotide has a $T_m$ of about 85-90° C. Still preferred, the $T_m$ of said oligonucleotide to a target gene at 1M monovalent cation concentration is about 65-90° C. The Gibbs free energy is measured between that part of the target gene that corresponds to the oligonucleotide, that part typically being the 5' UTR, 3'UTR, translational start site or the translational termination site.

The oligonucleotide sequence can be derived from any of the genes listed in Tables 1 and 2, or any other gene the modulation of whose expression is likely to produce a desirable therapeutic result in a muscle-wasting-associated condition. Table 3, 4 and 5 show representative antisense sequences that may be used in embodiments of the invention; these sequences are merely representative, and any sequence that acts as an antisense oligonucleotide and that modulates expression of a gene involved in a muscle-wasting condition may be used in compositions and methods of the invention.

In some embodiments, one or more of the antisense oligonucleotides of the invention is a modified oligonucleotide. Linkage and backbone modifications have shown a great promise for oligonucleotides to be used in vivo, such as 2'-O-methyls, 2'-O-allyls, locked nucleic acids and peptide nucleic acids.

In a preferred embodiment, the antisense oligonucleotides of the invention are modified to provide increased acid resistance as compared to unmodified oligonucleotide, or to provide increased resistance to endonuclease, or both. Further modifications are described below.

An antisense oligonucleotide can be constructed using chemical synthesis and enzymatic ligation reactions using procedures known in the art. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Although the specific antisense sequences described herein (e.g., in Tables 3, 4 and 5) depict the sequences as oligonucleotides containing only deoxyribonucleotide residues, it is to be understood that the present invention also includes embodiments wherein the oligonucleotides are composed of ribonucleotide residues (e.g., by substituting uridine for thymidine, and ribosyl substituents for deoxyribosyl substituents). Moreover, it is to be understood that the present invention also includes the embodiments in which the oligonucleotides are composed of only deoxyribonucleotide residues, of only ribonucleotide residues, or of mixtures of deoxyribonucleotide and ribonucleotide residues.

In some embodiments, antisense oligonucleotides of the present invention display greater than or equal to 60, 70, 80, 90, 95, or 99 percent sequence identity to a nucleotide sequence selected from the group of SEQ ID NO: 1-191.

The degree of similarity between two sequences can be determined using methods well known to the art (e.g., computer programs including Fasta (Oxford Molecular Group Inc.) and BLAST (www.ncbi.nlm.nih.gov) (Altschul et al. (1997) Nucleic Acid Res. 25, 3389-3402). These methods can be employed to take into account gaps in the sequences due to deletions or insertions. Homology or sequence identity at the nucleotide or amino acid sequence level determined by BLAST (Basic Local Alignment Search Tool) analysis uses the algorithm employed by the programs blastp, blastn, blastx, tblastn and tblastx (Altschul et al. (1997) Nucleic Acids Res. 25, 3389-3402 and Karlin et al. (1990) Proc. Natl. Acad. Sci. USA 87, 2264-2268, both fully incorporated by reference) which are tailored for sequence similarity searching. The approach used by the BLAST program is to first consider similar segments, with gaps (non-contiguous) and without gaps (contiguous), between a query sequence and a database sequence, then to evaluate the statistical significance of all matches that are identified and finally to summarize only those matches which satisfy a preselected threshold of significance.

In some embodiments the antisense oligonucleotides of the invention have a Guanine:Cytosine (GC content) greater than 35 percent. The GC content is preferably greater than 40 percent and most preferably, greater than 45 percent.

2. Ribozymes

"Ribozyme" refers to a nucleic acid molecule which is capable of cleaving a specific nucleic acid sequence. Ribozymes may be composed of RNA, DNA, nucleic acid analogues (e.g., phosphorothioates), or any combination of these (e.g., DNA/RNA chimerics). In some embodiments, a ribozyme refers to RNA molecules that contain anti-sense sequences for specific recognition, and an RNA-cleaving enzymatic activity.

As noted above, the present invention provides ribozymes having the ability to cleave or otherwise inhibit nucleic acid molecules which are either directly, or indirectly (e.g., they encode proteins) involved in muscle wasting disorders. Several different types of ribozymes may be constructed for use within the present invention, including for example, hammerhead ribozymes (Rossi, J. J. et al., Pharmac. Ther. 50:245-254, 1991) (Forster and Symons, Cell 48:211-220, 1987; Haseloff and Gerlach, Nature 328:596-600, 1988; Walbot and Bruening, Nature 334:196, 1988; Haseloff and Gerlach, Nature 334:585, 1988; Haseloff et al., U.S. Pat. No. 5,254,678), hairpin ribozymes (Hampel et al., Nucl. Acids Res. 18:299-304, 1990, and U.S. Pat. No. 5,254,678), hepatitis delta virus ribozymes (Perrotta and Been, Biochem. 31:16, 1992), Group I intron ribozymes (Cech et al., U.S. Pat. No. 4,987,071) and RNase P ribozymes (Takada et al., Cell 35:849, 1983); (see also, WO 95/29241, entitled "Ribozymes with Product Ejection by Strand Displacement"; and WO 95/31551, entitled "Novel Enzymatic RNA Molecules."

The sequence requirement at the cleavage site for the hammerhead ribozyme is any RNA sequence consisting of NUH (where N is any of G, U, C, or A and H represents C, U, or A) can be targeted. Accordingly, the same target within the hairpin leader sequence, GUC, is useful for the hammerhead ribozyme. The additional nucleotides of the hammerhead ribozyme or hairpin ribozyme is determined by the target flanking nucleotides and the hammerhead consensus sequence (see Ruffuer et al., Biochemistry 29:10695-10702, 1990).

Ribozymes, as well as DNA encoding such ribozymes and other suitable nucleic acid molecules, can be chemically synthesized using methods well known in the art for the synthesis of nucleic acid molecules (see e.g., Heidenreich et al., J FASEB 70(1):90-6, 1993; Sproat, Curr. Opin. Biotechnol. 4(1):20-28, 1993). Alternatively, commercial suppliers such as Promega, Madison, Wis., USA, provide a series of protocols suitable for the production of nucleic acid molecules such as ribozymes.

During synthesis, the ribozyme can be modified by ligation to a DNA molecule having the ability to stabilize the ribozyme and make it resistant to RNase (Rossi et al., Pharmac. Ther. 50:245-254, 1991). In another embodiment, the ribozyme can be modified to a phosphothio-analog for use in liposome delivery systems. This modification also renders the ribozyme resistant to endonuclease activity. In yet another embodiment, the ribozyme can be modified to contain propanediol linkages or to incorporate 2'-O-methylated nucleotides.

Any ribozyme that modulates expression of a gene involved in muscle wasting conditions, or that promotes muscle growth where muscle growth is desirable, e.g., the genes of Tables 1 and 2, may be used in the compositions and methods of the invention.

3. Interfering RNA (RNAi)

In another embodiment of the present invention, double stranded nucleic acids can be used to inhibit expression of genes associated with muscle wasting (e.g., myostatin and myostatin receptor genes) by RNA interference. RNA interference ("RNAi") is a mechanism of post-transcriptional gene silencing in which double-stranded RNA (dsRNA) corresponding to a gene (or coding region) of interest is introduced into a cell or an organism, resulting in degradation of the corresponding mRNA. The RNAi effect persists for multiple cell divisions before gene expression is regained. RNAi is therefore an extremely powerful method for making targeted knockouts or "knockdowns" at the RNA level. RNAi has proven successful in human cells, including human embryonic kidney and HeLa cells. See, e.g., Elbashir et al. Nature May 24, 2001;411(6836):494-8); Tuschl et al. (1999), Genes and Development 13:3191-3197; Zamore (2000), Cell 101:25-33, and U.S. Pat. No. 6,506,559, all of which are incorporated herein by reference in their entirety.

Thus, the invention further provides RNAi's that inhibit expression of genes involved in muscle wasting disease. In this connection, the invention provides an RNAi that modulates expression of myostatin or a myostatin receptor. As an example, this aspect of the invention provides small (less than about 50, or less than about 40, or less than about 30 or less than about 20 nt) dsRNA that specifically inhibits gene expression of genes involved in muscle wasting or in limiting muscle growth (reviewed in Caplen (2002) Trends in Biotechnology 20:49-51). In some embodiments, the RNAi includes: (a) double-stranded RNA of 21-25 nucleotides with overhangs of 2 nucleotides at both 3' ends; (b) 30-52% of the G+C content of the double stranded region; and (c) A/U base-pairing in positions 15-19 in sense strand; and (d) no internal repeats.

3. DNAzymes

Like RNAi, DNAzyme technology also represents an ideal choice for gene suppression. Such catalytic DNA molecules offer several advantages over ribozymes and are easier to synthesize at relatively low cost. Moreover, DNAzymes have a moderate-throughput capacity and act in a sequence-specific manner. This capacity for highly flexible binding and discrimination of nucleic acid substrates by virtue of Watson-Crick interactions enable DNAzymes to facilitate gene-type specific reactions for gene function validation with very high precision. See, e.g., Sun, L. Q., Cairns, M. J., Saravolac, E. G., Baker, A. and Gerlach, W. L. (2000) *Pharmacol. Rev.* 52(3), 325-347; and U.S. Pat. Nos. 6,617,438, 6,326,174, which are incorporated herein by reference in their entirety.

Thus, this aspect of the invention provides DNAzyme that inhibit expression of genes involved in muscle wasting disease. In some embodiments, the invention provides a DNAzyme that modulates expression of myostatin or a myostatin receptor. In some embodiments, the invention includes a DNAzyme that contains: (a) a catalytic domain that comprises the nucleotide sequence GGCTAGCTACAACGA (SEQ ID NO: 192) and that specifically cleaves mRNA coding for myostatin or a myostatin receptor at any purine:pyrimidine site to which the catalytic domain is directed, (b) a first binding domain contiguous with the 5'end of the catalytic domain, and (c) a second binding domain contiguous with the 3'end of the catalytic domain where each binding domain hybridizes with a region immediately flanking the cleavage site.

In some embodiments, the invention provides a composition that includes at least one antisense oligonucleotide targeted to myostatin and at least one antisense oligonucleotide targeted to a myostatin receptor, e.g., ARIIb. In some embodiments, the invention provides a composition that includes at least one antisense oligonucleotide targeted to human myostatin and at least one antisense oligonucleotide targeted to a human myostatin receptor, e.g., ARIIb. In some embodiments, the invention provides a composition that includes at least one antisense oligonucleotide targeted to human myostatin wherein the sequence of the oligonucleotide is selected from SEQ ID NOs 1-191 and at least one antisense oligonucleotide targeted to a myostatin receptor, e.g., ARIIb.

In some embodiments, the invention provides a composition that includes at least one antisense oligonucleotide targeted to myostatin and at least one antisense oligonucleotide targeted to a gene product that converts inactive myostatin to an active form, e.g., TLL2. In some embodiments, the invention provides a composition that includes at least one antisense oligonucleotide targeted to human myostatin and at least one antisense oligonucleotide targeted to a human gene product that converts inactive myostatin to an active form, e.g., TLL2. In some embodiments, the invention provides a composition that includes at least one antisense oligonucleotide targeted to human myostatin wherein the sequence of the oligonucleotide is selected from SEQ ID NOs 1-191 and at least one antisense oligonucleotide targeted to a gene product that converts inactive myostatin to an active form, human TLL2.

Any of these combinations may include a plurality of antisense oligonucleotides targeted to one or more of the target genes, e.g., combinations of oligonucleotides targeted to the 5' UTR, the 3'UTR, the start signal, coding sequences, and/or the termination signal, of one or more of the target genes.

B. Modifications of Nucleic Acids

The oligonucleotides that are employed in accordance with the present invention may be modified. An oligonucleotide that comprises at least one modification has one or more chemical modifications at the molecular level of the natural molecular structures of all or any of the nucleic acid bases, sugar moieties, internucleoside phosphate linkages, as well as molecules having added substituents, such as diamines, cholesteryl or other lipophilic groups, or a combination of modifications at these sites. For example, oligonucleotides can be end-blocked, protonated, exhibit substantial acid resistance, substantial nuclease resistance, and contain achiral internucleoside phosphate linkages and modified ribose or deoxyribose substituents.

The term "end-blocked" as used herein refers to a nucleic acid with a chemical modification at the molecular level that prevents the degradation of selected nucleotides, e.g., by exonuclease action. This chemical modification is positioned such that it protects the integral portion of the nucleic acid, for example the portion of an RNA or DNA that is chemically similar to the gene involved in the physiological condition. An end block may be a 3' end block, a 5' end block, or both. For example, a 3' end block may be at the 3'-most position of the molecule, or it may be internal to the 3' ends, provided it is 3' of the integral sequences of the nucleic acid.

The term "protonated compound" refers to a molecule of the invention that, when dissolved in water having a pH of 7 causes the pH of the solution to fall. Generally, compounds are protonated by adding protons to the reactive sites on the molecule, although other modifications of the molecule are possible, and are intended to be encompassed by this term. Such protonation can be accomplished, for example by incubating the compound in the presence of a strong acid, most preferably one with a volatile conjugate base. The term "protonation" and "acidification" as used interchangeably herein refers to the process by which protons (or positively charged hydrogen ions) are added to proton acceptor sites on a compound of the invention. The proton acceptor sites include the substituted or unsubstituted phosphates of the central group, as well as any additional proton acceptor sites on either the central group or the end blocking groups. As the pH of the solution is decreased, the number of these acceptor sites which are protonated increases, resulting in a more highly protonated compound.

Many nucleic acid backbones are not stable at low pH (e.g., pH 1-3) and experience depurination, although a number of backbones are relatively stable at pH 4-5. One aspect of the present invention reflects the recognition that certain modifications, including 2'-halide, 2'-O-alkyl, 3'-O-alkyl, and 2'-O-alkyl-n(O-alkyl) nucleic acid molecules are stable at the desired pH of 2 to 1. These modifications enhance the ability of the oligonucleotides of the pharmacological compositions of the present invention to affect a condition in vivo. Thus, the composition of the present invention may include nucleic acid molecules that are substantially acid resistant. The compositions of the present invention may also include nucleic acid molecules that are nuclease resistant. This includes nucleic acid molecules completely derivatized by 2'-O-methylphosphodiesters, 2'-O-alkyl, 2'-O-alkyl-n(O-alkyl), 2'-fluoro, 2'-deoxy-erythropentofuranosyl, chimeric linkages, and any other backbone modifications, as well as other modifications, which render the nucleic acid molecules substantially resistant to endogenous nuclease activity. Additional suitable methods of rendering nucleic acid molecules nuclease resistant include, but are not limited to, covalently modifying the purine or pyrimidine bases that comprise the nucleic acid. For example, bases may be methylated, hydroxymethylated, or otherwise substituted (e.g., glycosylated) such that the nucleic acid molecules comprising the modified bases are rendered substantially nuclease resistant. Nuclease resistance also aids the oligonucleotides of the compositions of the present invention in retaining their effect in vivo.

Preferably, the oligonucleotides of the of the present invention remain relatively unchanged chemically upon administration to a subject and retain their activity in acidic conditions (pH less than 6.0) or in the presence of an endonuclease or exonuclease (e.g., in an in vivo setting).

The term "substantially acid resistant" as used herein refers to nucleic acid molecules that are resistant to acid degradation as compared to unmodified nucleic acid molecules. Typically, the relative acid resistance of a nucleic acid will be measured by comparing the percent degradation of a resistant nucleic acid with the percent degradation of its unmodified counterpart (i.e., a corresponding nucleic acid of the same length and sequence having a "normal" backbone and bases). A nucleic acid that is acid resistant is preferably at least one and a half times more resistant to acid degradation, more preferably at least two times more resistant, even more preferably at least five times more resistant, and most preferably at least ten times more resistant than their unmodified counterpart.

Although certain acid resistant nucleic acid molecules exhibit marked acid stability and endonuclease resistance, they are sensitive to 3' exonucleases. In order to enhance the exonuclease resistance of 2'-O-alkyl substituted nucleic acid molecules, the 3' or 5' and 3' ends of the nucleic acid are preferably attached to a chemical moiety that provides an exonuclease blocking function. For example, one or more phosphorothioate nucleotides can be placed at either end of the RNA or DNA. Additionally, one or more inverted bases can be placed on either end of the RNA or DNA, or one or more alkyl or alcohol (e.g., butanol-substituted) nucleotides or chemical groups can be placed on one or both ends. Accordingly, a preferred embodiment of the present invention is a nucleic acid comprising a nucleic acid having the following structure: A-B-C, wherein "B" is a 2'-O-alkyl or 2'-O-alkyl-n(O-alkyl) substituted RNA between about 1 and about 98 bases in length, and "A" and "C" are respective 5' and 3' end blocking groups (e.g., one or more phosphorothioate nucleotides (but typically fewer than six), inverted base linkages, or alkyl, alkenyl, alkynyl, O-alkyl, and O-alkyl-n (O-alkyl) groups or substituted nucleotides). A partial list of blocking groups includes inverted bases, dideoxynucleotides, methylphosphates, alkyl groups, aryl groups, cordycepin, cytosine arabanoside, 2'-methoxy, ethoxy nucleotides, phosphoramidates, a peptide linkage, dinitrophenyl group, 2'- or 3'-O-methyl bases with phosphorothioate linkages, 3'-O-methyl bases, fluorescein, cholesterol, biotin, acridine, rhodamine, psoralen, glyceryl, methyl phosphonates, butanol, butyl, hexanol, and 3'-O-alkyls. An enzyme-resistant butanol preferably has the structure OH—$CH_2CH_2CH_2CH_2$ (4-hydroxybutyl), which is also referred to as a C4 spacer.

The term "substantially nuclease resistant" refers to nucleic acid molecules that are resistant to nuclease degradation, as compared to naturally occurring or unmodified nucleic acid molecules. Modified oligonucleotides of the invention are at least 1.25 times more resistant to nuclease degradation than an unmodified nucleic acid having the same sequence and number of nucleotides, more preferably at least 2 times more resistant, even more preferably at least 5 times more resistant, and most preferably at least 10 times more resistant than their unmodified counterpart. Such substantially nuclease resistant nucleic acid molecules include, but are not limited to, nucleic acid molecules with modified backbones such as ethylphosphotriesters, 2'-O-methylphosphorothioates, 2'-O-methyl-p-ethoxy ribonucleotides, 2'-O-alkyls, 2'-O-alkyl-n(O-alkyl), 2'-fluoros, 2'-deoxy-erythropentofuranosyls, 2'-O-methyl ribonucleosides, 3'-O-methylribonucleotides, inverted bases (e.g., inverted T's), or chimeric versions of these backbones.

The modified oligonucleotide includes RNA or DNA comprising modifications to the sugar moieties such as 2'-substituted or 3'-substituted ribonucleotides, or deoxyribonucleotide monomers, any of which are connected together via internucleoside linkages. Modified RNA or DNA may also be comprised of PNA or morpholino modified backbones where specificity of the sequence is maintained.

The ribose groups and the internucleoside linkages link the bases in a nucleic acid and are referred to as the nucleic acid backbone. A modified backbone includes modifications to the chemical linkage between nucleotides, as well as other modifications that may be used to enhance stability and affinity, such as modifications to the sugar structure. For example, an L-anomer of deoxyribose may be used, where the base is inverted with respect to the natural D-anomer. In one embodiment, the 2'-OH of the sugar group may be altered to 2'-halogen, 2'-O-alkyl or 2'-O-alkyl-n(O-alkyl), which provides resistance to degradation without compromising affinity. Other suitable modified backbones include the following types of internucleotide linkages: 2'-O-methyl-phosphodiesters, 2'-O-alkyl, 2'-O-ethyl, 2'-O-propyl, 2'-O-butyl, 2'-O-alkyl-n(O-alkyl), 2'-methoxyethoxy, 2'-fluoro, 2'-deoxy-erythropentofuranosyl, 3'-O-methyl, p-isopropyl oligonucleotides, 2'-O($CH_2CH_2)_xCH_3$, and/or butyne linkages. An oligonucleotide may have combinations of such modified backbones, may be completely modified, or may comprise all or some linkages being phosphodiester linkages.

Preferred internucleoside linkages on the modified oligonucleotide are achiral. The term "achiral" as used herein, refers to a molecule that is superimposable with its mirror image, whereas the term "chiral" refers to a molecule that is not superimposable with its mirror image. Oligonucleotides containing achiral 5' to 3' internucleoside phosphate linkages have internucleotide linkages which are achiral (i.e., no stereochemistry). The achiral oligonucleotides preferably contain at least about three to eight contiguous achiral internucleoside linkages, more preferably, nine to ten contiguous achiral internucleoside linkages, even more preferably, eleven to twelve contiguous achiral internucleoside linkages, and most preferably, is completely comprised of achiral internucleoside linkages through the entire contiguous sequence. In another embodiment, the achiral internucleoside linkages are interspersed with chiral internucleoside linkages (e.g., two contiguous achiral linkages followed by one chiral linkage followed by two contiguous achiral linkages; three contiguous achiral linkages followed by one chiral linkage; four contiguous achiral linkages followed by two achiral linkages, etc.). Examples of achiral internucleoside linkages include, but are not limited to, phosphodiester and diphosphorothioate linkages. Achiral RNA and DNA linkages in the backbone are routinely generated during automated synthesis of oligonucleotides if the final structure is a symmetrical molecule (i.e., a phosphate with the same atom attached to both sides).

The internucleoside phosphate linkages can be phosphodiester, or 3' to 3', 5' to 2' or 5' to 5' linkages, and combinations of such similar linkages (to produce mixed backbone modified RNA or DNA). The modifications can be internal (single or repeated) or at the end(s) of the RNA or DNA molecule. These modifications can include additions to the nucleic acid molecule, such as cholesteryl, diamine compounds with varying numbers of carbon residues between amino groups and terminal ribose, and deoxyribose or phosphate modifications which cleave or cross-link to the opposite chains or to associated enzymes or other proteins. Electrophilic groups such as ribose-dialdehyde could covalently link with an epsilon amino group of the lysyl-residue of such a protein. A nucleophilic group such as n-ethylmaleimide tethered to an RNA or DNA could covalently attach to the 5' end of an mRNA or to another electrophilic site Efficacy of a particular composition may be determined by means known in the art. These include in vitro and in vivo methods, such as, e.g., analysis of expression in cell culture contacted with the compositions, analysis of expression and/or phenotypic characteristics and/or physiological characteristics in an in vivo model, and clinical trials. In vivo models include established animal models for various disorders, as well as normal animals which are tested to determine the effect of a composition. For myostatin and muscle growth regulating compositions, model systems such as those provided in the Examples may be used.

C. Compositions

Compositions of the present invention include compositions that contain a single gene-expression modulating oligonucleotide or combinations of gene-expression modulating oligonucleotides. The oligonucleotides are directed at genes involved in muscle-wasting disorders and/or genes that promote muscle growth where muscle growth is desired. Compositions may include only one type of oligonucleotide, e.g., only antisense oligonucleotides. Compositions may include more than one type (e.g., any combination of antisense oligonucleotides, RNAi, ribozymes, and/or DNAzymes). Compositions may include multiple oligonucleotides directed against multiple areas of a single gene. For example, in some embodiments, the invention provides combinations of oligonucleotides, e.g., antisense oligonucleotides, that target the 5' untranslated region (UTR), the 3'UTR, the start, and/or the termination signal of an mRNA derived from a gene. In some embodiments the gene is a myostatin gene. Compositions may include multiple oligonucleotides directed against more than one gene. Compositions may include multiple oligonucleotides directed against multiple areas of multiple genes.

The compositions of the invention typically include more than about one, two, three, four, five, six, seven, eight, nine, 10, 15, 20, 30, 40, 50, 75, or 100 different oligonucleotides. Preferably, the compositions of the invention include about two to about 20 different oligonucleotides. More preferably, the compositions of the invention include about two to about 15 different oligonucleotides, and most preferably, the compositions of the invention include about two to about 10 different oligonucleotides; or alternatively, compositions of the invention include about two to about eight different oligonucleotides or about two to about six different oligonucleotides. In some embodiment, compositions of the invention include about two to about four different oligonucleotides. Thus, in some embodiments, the invention provides combinations of two or more oligonucleotides targeted to modulating expression of two or more different genes involved in muscle wasting conditions. Exemplary genes to which the antisense oligonucleotides may be directed are listed in Tables 1 and 2. In some embodiments, the invention provides combinations of two or more oligonucleotides, where the oligonucleotides are selected from the group consisting of antisense oligonucleotides, RNAi, ribozymes; and DNAzymes, that are targeted to modulating expression of two or more different genes involved in muscle wasting conditions, where the genes are selected from those listed in Tables 1 and 2.

In some embodiments, the invention provides RNAi to myostatin, myostatin receptors, and/or other genes involved in muscle wasting conditions. In some embodiments, the invention provides a combination of RNAis, where the RNAis are inhibitory to at least two of the genes listed in Tables 1 and 2. In some embodiments, the invention provides ribozymes to myostatin, myostatin receptors, and/or other genes involved in muscle wasting conditions. In some embodiments, the invention provides a combination of ribozymes, where the ribozymes are inhibitory to at least two of the genes listed in Tables 1 and 2. In some embodiments, the invention provides DNAzymes to myostatin, myostatin receptors, and/or other genes involved in muscle wasting conditions. In some embodiments, the invention provides a combination of DNAzymes, where the DNAzymes are inhibitory to at least two of the genes listed in Tables 1 and 2.

In some embodiments, the invention provides one or more antisense oligonucleotides to myostatin. In some embodiments, the invention provides a combination of antisense oligonucleotides to myostatin that includes at least two different antisense oligonucleotides to myostatin. In some embodiments, the myostatin is selected from the group consisting of human, cow, pig, chicken, mouse, horse, dog, and fish myostatin. In some embodiments, the invention provides a combination of antisense oligonucleotides to different parts of the human myostatin gene transcript, including at least two antisense oligonucleotides targeted to portions of the transcript selected from the group consisting of the 5' UTR, the 3' UTR, the start, and the termination signal. In some embodiments, the invention provides a combination of antisense oligonucleotides to human myostatin, including at least two antisense oligonucleotides selected from the group consisting of SEQ ID NOS. 1-191.

In some embodiments, the invention provides a composition that includes at least one antisense oligonucleotide targeted to myostatin and at least one antisense oligonucleotide targeted to at least one non-myostatin gene selected from those listed in Tables 1 and 2. Some embodiments provide combinations of antisense oligonucleotides targeted to myostatin and to two or more other genes listed in Tables 1 and 2. In some embodiments, the invention provides a composition that includes at least one antisense oligonucleotide targeted to myostatin and at least one antisense oligonucleotide targeted to at least one of NFκB, Cox 2, myo D, a myostatin receptor (e.g., ARIIb), and/or a gene product that converts inactive myostatin to an active form (e.g., TLL2).

In some embodiments, the invention provides a composition that includes at least one antisense oligonucleotide targeted to myostatin and at least one antisense oligonucleotide targeted to myo D. The myostatin and myoD are human in preferred embodiments. In some embodiments, the invention provides a composition that includes at least one antisense oligonucleotide targeted to human myostatin, wherein the sequence of the oligonucleotide is selected from SEQ ID NOs 1-191.

Any of these combinations may include a plurality of antisense oligonucleotides targeted to one or more of the target genes, e.g., combinations of oligonucleotides targeted to the 5' UTR, the 3'UTR, the start signal, and/or the termination signal, of one or more of the target genes.

D. Pharmaceutical, Nutritional Supplement, and Homeopathic Compositions

The invention further provides pharmaceutical, nutritional supplement, and homeopathic compositions.

Pharmaceutical compositions The present invention includes pharmaceutical compositions comprising at least about one oligonucleotide as described herein. In some embodiments, the invention provides pharmaceutical compositions that include at least two, three, four, five, six, seven, eight, nine, 10, 15, 20, 30, 40, 50, 75, or 100 different oligonucleotides, as described herein. In some embodiments, the oligonucleotides are antisense oligonucleotides, ribozymes, siRNA, DNAzymes, or a combination thereof. In some embodiments, one or more of the oligonucleotides is a modified oligonucleotide. In some embodiments, the pharmaceutical composition contains one or more antisense oligonucleotides, any or all of which may be modified as described herein. The pharmaceutical compositions further comprise a pharmaceutically suitable excipient.

As used herein, the term "pharmaceutical composition" refers to a therapeutic composition that is used to treat a particular disease or pathological disorder that is suitable for parenteral, oral or topical administration in humans.

The compositions containing the oligonucleotides of the invention in an admixture with a pharmaceutically acceptable carrier can be prepared according to known techniques. The carrier may take a wide variety of forms depending on the form of preparation desired for administration, e.g., intravenous, oral, topical, aerosol (for topical or inhalation therapy), suppository, parenteral, or spinal injection. The excipient may contain any number of carriers. In the case of homeopathic pharmaceuticals the carriers would preferably be homeopathic carriers, e.g., homeopathic agents that may increase the efficacy of the homeopathic composition or help to alleviate symptoms associated with a physiological condition. In addition, the composition may contain stabilizers, preservatives, and other ingredients, preferably in amounts from about 0.5 to 2.0 percent by weight, provided they do not adversely affect the ability of the pharmacological composition to treat the physiological condition. It is well within the skill of one in the art to determine an appropriate mode of administration and to select an appropriate delivery system.

Administration of the composition will introduce the modified oligonucleotides to the individual in a diluted amount. Exemplary unit dosages for oral or topical administration may be more than about 0.01, 0.05, 0.1, 0.5, 1, or 5 mg/kg, and/or less than about 10, 5, 1, 0.5, 0.1, or 0.05 mg/kg. Exemplary unit dosage ranges may be between about 0.01 mg/kg and 10 mg/kg, or between about 0.010 mg/kg and 1.0 mg/kg, or between about 0.10 mg/kg and 1.0 mg/kg for a composition that contains a single oligonucleotide. In some embodiments, the oligonucleotide compositions of the present invention are administered at unit dosages of about 0.01 to about 100 ug per kg of body weight, or about 0.1 to about 100 ug per kg of body weight, or about 0.1 to about 10 ug per kg of body weight, or about 1 to about 10 ug per kg of body weight, or about 1 to about 5 ug per kg of body weight. When more than one oligonucleotide is present in the composition, dosages of each oligonucleotide may be in the latter ranges, or dosage of one or more of the oligonucleotides may be decreased, based on the expected overall effect of the combination. In some embodiments, unit dosages per single oligonucleotide are at or below 100 ug per kg of body weight, or at or below 10 ug per kg of body weight, or at or below 1 ug per kg of body weight, or at or below 0.1 ug per kg of body weight, or at or below 0.01 ug per kg of body weight.

When orally administered, one dosage unit may be administered once every 10, 9, 8, 7, 6, 5, 4, 3, 2, or one day, or 1, 2, 3, 4, 5, 6, 7, 8, 9, 10, or more than 10 times per day until relief is achieved or until the symptoms disappear or are satisfactorily attenuated. In some embodiments, one dosage unit is administered about once to about four times per day. In some embodiments, a patient is instructed to orally take two to three dosage units per day. The dosage unit may be placed under the tongue of the patient-or simply swallowed for such oral administration.

The pharmaceutical compositions of the present invention may be formulated for administration to humans and animals in liquid form, or in tablets, pills, granules, powders, or in ointments, creams, injectables, or suppositories. Ointments and creams are impregnated with a low liquid potency or, sometimes, mother tinctures and are generally prescribed as specific remedies. Liquid compositions may be supplied in amber glass dropper bottles to protect them from light.

In preparing the compositions in oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs, and solutions); or carriers such as starches, sugars, diluents, granulating agents, lubricants, binders, disintegrating agents and the like in the case of oral solid preparations (such as, for example, powders; capsules and tablets).

For administration by injection, preparations may comprise an aqueous solution of a water soluble, or solubilized, and pharmacologically acceptable form of the nucleic acid in an appropriate liquid, e.g., water or saline solution. Injectable suspensions may also be prepared using appropriate liquid carriers, suspending agents, agents for adjusting the isotonicity, preserving agents, and the like. Actual methods for preparing administrable pharmacological compositions and adjustments necessary for administration to subjects will be known or apparent to those skilled in the art.

For topical administration, the carrier may take a wide variety of forms depending on the preparation, which may be a cream, dressing, gel, lotion, ointment, or liquid. A surfactant can be included in the composition to provide deeper penetration of the ingredients. Although natural surfactants are preferred, others such as isopropyl myristate can be used. In one embodiment, the composition is a cosmetic composition for topical administration to the skin. As used herein, the term "cosmetic composition" refers to a composition that is applied topically to the skin to improve the appearance of the skin.

Aerosols are prepared by dissolving or suspending the nucleic acid in a propellant such as ethyl alcohol or in propellant and solvent phases. The pharmaceutical compositions for topical or aerosol form will generally contain from about 0.001 percent by weight (of the nucleic acid) to about 40 percent by weight, preferably about 0.02 percent to about 10 percent by weight, and more preferably about 0.05 percent to about 5 percent by weight depending on the particular form employed. Suppositories are prepared by mixing the nucleic acid with a lipid vehicle such as theobroma oil, cacao butter, glycerin, gelatin, or polyoxyethylene glycols.

The nucleic acid molecule(s) may be combined with a lipid, cationic lipid, or anionic lipid and the active agent delivered via a nucleic acid/lipid emulsion, or a liposomal suspension. By assembling nucleic acid molecules into lipid-associated structures, the nucleic acid molecules may exhibit an increased half-life in vivo. Examples of suitable anionic lipids for use with RNA or DNA include, but are not limited to, cardiolipin, dimyristoyl, dipalmitoyl, or dioleoyl phosphatidyl choline or phosphatidyl glycerol, palmitoyloleoyl phosphatidyl choline or phosphatidyl glycerol, phosphatidic acid, lysophosphatidic acid, phosphatidyl serine, phosphatidyl inositol, and anionic forms of cholesterol.

Nutritional supplements As used herein, the term "nutritional supplement" refers to a composition that is intended to supplement the diet. A nutritional supplement includes any dietary substance used in mammals to supplement the diet by increasing total dietary intake; or a concentrate, metabolite, constituent, extract, etc. Nutritional supplement includes any product that is intended for ingestion in tablet, capsule, powder, soft-gel, gel-cap, or liquid form. As used herein, the term "nutritional supplement" is used synonymously with the term "dietary supplement" and "nutraceutical" throughout the specification.

The present invention provides a composition which is useful as a nutritional supplement generally, and specifically for those suffering from a muscle wasting condition.

The nutritional supplement composition of the present invention include compositions with a single oligonucleotide and/or a combination of about two or more oligonucleotides. The oligonucleotides or combinations of oligonucleotides may be any of those described herein. The use of the nutritional supplement compositions of the present invention can be used to treat any of the aforementioned indications. These agents may be combined in an oral dosage with other well known nutritional supplements and/or non-flavonoid antioxidants (e.g., selenium, vitamin E (tocopherol, particularly alpha-tocopherol), vitamin C (ascorbic acid) and coenzyme Q10). Dietary fiber supplements may also be used in the composition.

Other additives may be incorporated in the nutritional supplement of the present invention. Such additives include minerals, (e.g., boron, etc. and trace metals such as zinc, magnesium, manganese, chromium, molybdenum, copper, iron, calcium, and potassium; and other micronutrients such as thiamine, riboflavin, niacin, pantothenic acid, pyridoxine, choline, biotin, inositol, para-aminobenzoic acid, vitamin D, vitamin K, vitamin A). In another embodiment of the invention a dietary fiber supplement such as oat bran or other natural fiber source may also be added to the composition.

Typically the nutritional supplement will further include a pharmaceutically acceptable carrier such as lactose, glucose, sucrose, corn starch, potato starch, cellulose acetate, ethyl cellulose, etc. Diluents and other additives such as one or more pharmaceutically acceptable binding agents, fillers, supports, thickening agents, taste-improving agents, coloring agents, preservatives, stabilizers, regulators, emulsifiers or mixtures thereof may be used depending on the form of the composition employed.

In addition to providing the aforementioned compositions, the invention also includes a method for orally administering the nutritional supplement composition in dosages effective to aid in the maintenance and improvement of an individual's health. The supplement is preferably administered orally. Suitable forms for the nutritional supplement composition for oral administration include tablets, capsules, lozenges, syrups, granules, solutions and suspensions which contain unit doses of the supplement for administration once or several times a day. The nutritional supplement composition of the invention will typically be administered orally as a liquid, tablet or a capsule. Tablets, gel tabs, capsules, liquid and sustained release formulations can be formulated and prepared according to manufacturing techniques well known in the pharmaceutical industry and in a variety of dosage forms.

The amount of oligonucleotides of the invention that is contained in a nutritional supplement depends on the desired nutritional effect. As the modified oligonucleotides described herein are generally very well tolerated, large amounts may be given in the form of nutritional supplements. Exemplary dosages include about 0.1 mg/kg to 100 mg/kg per day, or between about 1.0 mg/kg and 50 mg/kg per day, or between about 1.0 and 20 mg/kg per day. As described above, when combinations of oligonucleotides are used, dosages of individual oligonucleotides in the nutritional supplement may be adjusted downward if necessary or desirable. Nutritional supplements of the invention may include modified oligonucleotides, as described herein.

Homeopathic compositions In some embodiments, the invention provides homeopathic compositions. Homeopathic compositions may be made by methods known in the art. One exemplary method of making a homeopathic composition comprises (i) triturating solid oligonucleotide of the invention in a 1/9 ratio with lactose to produce a 1× solid and (ii) repeating the process until the desired attenuation is achieved. In a related vein, a method of making a homeopathic composition comprising (i) dissolving 1 part oligonucleotide of the invention by weight in liquid to produce ten volumes of liquid attenuation labeled 1× and optionally (ii) mixing 1 ml of the 1× attenuation with 9 ml of diluent to produce a lower concentration, is also addressed.

In some embodiments, the invention includes homeopathic compositions containing modified oligonucleotides. Any oligonucleotide or combination of oligonucleotides described herein may be used in the homeopathic compositions. In one embodiment, tablets for homeopathic use are preferably produced as placebo tablets that are then medicated by dripping or spraying liquid potencies onto the tablets in such a manner as to ensure a coefficient of impregnation of almost 100 percent. The placebo tablets are preferably formed by compression. Pills or granules are preferably spherical in shape, of about 4 millimeters diameter and 3 to 5 centigrams in weight. They are preferably prepared (from pure lactose) and medicated in the same manner as tablets. For example, solid oligonucleotides or combinations of oligonucleotides can be triturated (i.e., ground up) in a 1/9 ratio with lactose (1 gram of oligonucleotide+9 grams of lactose) to produce a 1× solid. The process is repeated (1 gram of that material plus 9 grams of lactose) until the desired attenuation is achieved.

For homeopathic compositions, the excipient may contain any number of carriers, and preferably homeopathic carriers, e.g., homeopathic agents that may increase the efficacy of the homeopathic composition or help to alleviate symptoms associated with a physiological condition. For example, oligonucleotides or combinations of oligonucleotides can be dissolved in a liquid 1 part by weight to produce a ten volumes of liquid attenuation labeled 1×. To produce lower dilutions 1 ml of the 1× attenuation is used (mixed thoroughly) with 9 ml of diluent to produce 2×. This process is repeated until the desired attenuation is achieved. A homeopathic carrier solution such as that described in U.S. Pat. No. 5,603,915 may be used for increasing the efficacy of the homeopathic agent. This carrier solution is sequentially subjected to an alternating current electrical treatment and a direct current electrical treatment, after which additional ingredients such as seawater, brain hormones, and biologically active enzymes are added. The electrical treatment of the carrier, along with the addition of homeopathically active substances, can be used to increase the efficacy of the homeopathic composition. Alternatively, an electromagnetic carrier, such as described in U.S. Pat. No. 5,830,140 may be employed. For homeopathic preparations for example, oligonucleotides or combinations of oligonucleotides can be dissolved in a liquid 1 part by weight to produce a ten volumes of liquid attenuation labeled 1×. To produce lower dilutions 1 ml of the 1× attenuation is used (mixed thoroughly) with 9 ml of diluent to produce 2×. This process is repeated until the desired attenuation is achieved. Typical homeopathic unit doses are given in Table 7.

II. Methods of the Invention

The invention further provides methods of treatment using the compositions of the invention. Methods include methods of modulating gene expression in cells by contacting cells with compositions of the invention. Methods also include methods of treatment of muscle wasting disorders or conditions. As used herein, the term "muscle wasting disorder," used synonymously herein with the term "muscle wasting condition," encompasses disorders or conditions in which muscle wasting is one of the primary symptoms, such as muscular dystrophy, spinal cord injury, neurodegenerative diseases, anorexia, sarcopenia, cachexia, muscular atrophy due to immobilization, prolonged bed rest, or weightlessness, and the like, as well as disorders in which an abnormally high fat-to-muscle ratio is implicated in a disease or pre-disease state, e.g., Type II diabetes or Syndrome X. Methods include allopathic, nutritional, and homeopathic therapeutic methods. Conventional means of diagnosis may be used to determine the presence and severity of these conditions. In addition, the invention provides methods of increasing muscle mass in animals where such an increase is desirable, e.g., in food animals such as mammals and fish. Also, the compositions described herein can be used as an adjunct to other therapies e.g. those employing other therapeutic agents, dietary modifications, physical therapy, and the like.

Atrophy of skeletal muscle occurs in muscles of adult animals as a result of lack of use, aging, starvation, and as a consequence of a variety of diseases, disorders, and conditions such as sepsis, muscular dystrophy, AIDS, aging, and cancer. The loss of muscle is generally characterized by decreases in protein content, force production, fatigue resistance, and muscle fiber diameter. These decreases can be attributed to both a decrease in protein synthesis and an increase in protein degradation. Muscle wasting and related conditions to which the compositions and methods of the invention are directed include any condition in which enhanced muscle growth, or diminishment of muscle wasting, produces a therapeutically or otherwise desirable result. Conditions include muscular dystrophy, sarcopenia, cachexia, diabetes mellitus, and the improvement of muscle mass where such improvement is ethical and desirable, e.g., in food animals.

Diseases associated with muscle wasting generally are associated with altered or abnormal expression of a number of genes compared to the normal state. As used herein, the term "abnormal," when used in reference to the amount, development or metabolic activity of muscle or adipose tissue, is used in a relative sense in comparison to an amount, development or metabolic activity that a skilled clinician or other relevant artisan would recognize as being normal or ideal. Such normal or ideal values are known to the clinician and are based on average values generally observed or desired in a healthy individual in a corresponding population. For example, in patients with obesity-related diseases such as diabetes, the clinician would know that obesity is associated with a body weight that is about twenty percent above an "ideal" weight range for a person of a particular height and body type. However, the clinician would recognize that a body builder is not necessarily obese simply by virtue of having a body weight that is twenty percent or more above the weight expected for a person of the same height and body type in an otherwise corresponding population. Similarly, the artisan would know that a patient presenting what appears to abnormally decreased muscle activity could be identified as having abnormal muscle development, for example, by subjecting the patient to various strength tests and comparing the results with those expected for an average healthy individual in a corresponding population.

The compositions and methods of the invention target individual genes as well as, preferably, combinations of genes involved in these conditions. By employing combination compositions and therapies, reversible reactions may be avoided, and multiple pathways may be targeted simultaneously, leading to greater therapeutic effect than when single genes are targeted. Toxicity, if any, may be lower by using combination therapies due to potentially lower amounts of each particular gene modulator being used. In addition, combinations of inhibitors, and combinations of targets in single genes are encompassed by the methods of the invention. In general, gene modulators used in compositions and methods of the invention are targeted at genes whose expression is desired to be inhibited; however, in some cases, some of the gene modulators used in embodiments of the invention may result in an increase in expression.

The invention also encompasses modified oligonucleotides for use in gene modulation, where the modified oligonucleotides are typically more stable and resistant to degradation than natural oligonucleotides; the modified oligonucleotides of the present invention are less toxic than many presently-used modifications (e.g., S-oligonucleotides), thus allowing dosages to be higher without adverse side effects.

A. Muscle Wasting Conditions

The compositions and methods of the invention are of use in conditions where muscle wasting occurs, and/or where increased muscle mass and/or decreased fat mass is desirable. Exemplary conditions of mammals that may be treated by the compositions and methods of the invention include, but are not limited to:

Muscular dystrophy The muscular dystrophies are a heterogeneous group of neuromuscular disorders. The diseases include the most common type, Duchenne muscular dystrophy (DMD), multiple types of limb girdle MD (LGMD) and other congenital MDs (CMD). Progressive muscle damage and muscle loss, tissue inflammation and replacement of healthy muscle with fibrous and fatty tissues result in muscle wasting in muscular dystrophy. Extreme muscle loss is one of the most prominent signs of the disease, and leads to complications and symptoms, including death.

Sarcopenia Sarcopenia is the age-related loss of muscle mass, strength and function. It begins in the fourth decade of life and accelerates after the age of approximately 75 years. Many factors, including physical inactivity, motor-unit remodeling, decreased hormone levels, and decreased protein synthesis, may all contribute to sarcopenia. With the exception of physical inactivity, all of these may be subject to genetic control where gene modulation may be useful. For example, the rate of muscle protein synthesis and protein breakdown affects sarcopenia. The balance of protein synthesis and breakdown determines the protein content in the body. Research has consistently reported that muscle protein synthesis rates are lower in older adults when compared to younger adults. A decrease in muscle protein catabolism, effected by, e.g., gene modulation, could result in slowing or reversal of the loss of muscle mass.

Cachexia Cachexia is a condition associated with a variety of serious diseases, including cancer, AIDS, septicemia and congestive heart failure. Its major effect is massive loss of both adipose tissue and skeletal muscle, which is not caused by malnutrition. Cachexia contributes to nearly one-third-of all cancer deaths. In a process that is not yet well understood, cytokines and tumor factors mediate wasting by suppressing muscle gene products. Cachectic factors have been shown to be selective in targeting the myosin heavy chain. In myotubes and mouse muscles, TNF-alpha plus IFN-gamma strongly reduced myosin expression through an RNA-dependent mechanism. Cachexia involves a complex disruption of several systems that also leads to anemia, insulin resistance, immunosuppression, and activation of an acute-phase response. See, e.g., Acharyya et al., J. Clin. Invest. 114:370-78 (2004). The resulting progressive weakness can make patients with cancer more susceptible to the toxic effects of radiation and chemotherapy; many such patients die from cachexia-related syndromes, rather than from their tumors. Thus, the therapies of the present invention aimed at reversal of muscle wasting in cachexia are considered one promising approach to the condition.

Diabetes Diabetes mellitus is the most common of the serious metabolic diseases. Obesity and a high body mass index (BMI) are risk factors for diabetes. Type I diabetes, also known as juvenile-onset diabetes, results from destruction of the beta-cells of the pancreas, and generally requires exogenous administration of insulin for treatment. Type II diabetes, also known as adult-onset diabetes, accounts for over 80% of the cases of diabetes, and its incidence is increasing at a rapid rate. In Type II diabetes, onset is generally gradual and is related to a number of factors, including obesity. Type II diabetes can often be ameliorated and in some cases controlled through lifestyle changes, which can include weight loss and increase in skeletal muscle mass. Studies in transgenic mice have shown that alterations in muscle mass and body composition induced by modulation of gene activity can alter the parameters associated with diabetes. For example, the dramatic reduction in overall fat accumulation in myostatin mutant mice as compared to wild type mice indicates that myostatin activity can be manipulated to treat or prevent obesity or type II diabetes. See, e.g., U.S. Pat. No. 6,656,475, incorporated by reference herein in its entirety.

It will be appreciated by those of skill in the art that the above conditions are merely exemplary of conditions in which modulation of genes involved in muscle wasting by the compositions and methods of the invention may be effective. Other disorders that may be treated by modulation of gene expression involved in muscle wasting include, but are not limited to, spinal cord injury, neurodegenerative disorders, traumatic injury, congestive obstructive pulmonary disease (COPD), anorexia, AIDS, atrophy due to immobilization, bed rest, or weightlessness, and any other disorder in which there is a disruption of normal skeletal muscle mass or strength. In accordance with the present invention, genes whose expression is altered in these disorders, or whose modulation would achieve therapeutic benefit even if their expression is not directly altered, e.g., myostatin, myostatin regulatory elements, and the like, may be modulated to achieve muscle specific expression of a target gene to promote muscle growth and increase muscle mass for the treatment of a muscle associated disorder. Other genes that are abnormally expressed, or whose modulated expression promotes a therapeutic effect for the condition, may be separately or simultaneously modulated by the methods and compositions of the invention.

B. Gene Targets for Therapy

Gene targets for therapy include, but are not limited to, those genes summarized in Tables 1 and 2, and described more fully below.

Myostatin Myostatin is a major gene involved in regulating muscle growth that may be involved, directly or indirectly, in almost every muscle wasting condition. As a secreted growth factor, myostatin acts as a negative regulator of skeletal muscle mass in mammals and other animals. Myostatin is almost exclusively expressed in the skeletal muscle lineage, where it negatively regulates myocyte differentiation/growth and determines muscle size. It is a member of the transforming growth factor β family and is expressed in both developing and adult muscles. During development, myostatin is initially expressed in the myotome layer of somites, which give rise to skeletal muscle. In adults, myostatin is expressed in all skeletal muscles. Mice lacking the myostatin gene have 25-30% increased muscle mass. See, e.g., McPherron et al., (1997) *Nature*, 387 (6628), 83-90. Individual muscles, such as the pectoralis and quadriceps, of myostatin mutant mice are 2-3-fold heavier than those of wild type mice. See, e.g., Whittemore et al. (2003) *Biochem. Biophys. Res. Commun.*, 300(4), 965-971, and Grobet et al. (2003) *Genesis*, 35(4), 227-238.

This modulation occurs both in early development and in adults. Blockage of myostatin function in adult mice using a myostatin antibody or conditional knockout technology results in the increment of muscle mass. Like endocrine hormones, myostatin circulates in the serum in high amounts. An increased level of myostatin has been reported in disease conditions with muscle wasting. Thus, myostatin is regarded as a unique drug target and therapeutics that modulate skeletal muscle growth would be useful for disease conditions such as muscular dystrophy, sarcopenia, cachexia, diabetes, and similar muscle-wasting disorders.

Recently, antibody mediated myostatin blockage in mdx mice was employed for the improvement of dystrophy. Blocking myostatin in mdx mice not only increased the number of normal muscle cells but also augmented muscle strength. The mechanism by which myostatin blockage resulted in the recovery of muscle function is not clear, but, without being limited by theory, it is proposed that balancing the muscle loss by wasting with increased muscle mass by myostatin blockage would be beneficial for dystrophic muscles. Since myostatin blockage is effective for increment of muscle mass even in adults, myostatin blockers are also promising as a treatment for dystrophy and other muscle wasting diseases.

In sarcopenia, serum myostatin increases in human aging associated with muscle wasting, and has been viewed as a biomarker of age associated sarcopenia. The human myostatin gene product is proposed to be a suppressor of skeletal muscle growth with advancing age. Thus, myostatin blockage would be beneficial for preventing sarcopenia.

In addition, even if myostatin is not directly implicated in a disorder, its modulation is useful in that it may serve as an alternative pathway for stimulating muscle growth, bypassing a pathway that may be blocked or modified in a particular disorder.

Myostatin receptors Signaling of myostatin is similar to that of activins and TGF-β. It efficiently binds the type II receptor ActRIIB and forms a heteromeric complex with the type I receptor ALK4 or ALK5, which leads to phosphorylation of the members of Smad family to control gene transcription and mediates the effects of myostatin. Smads are a family of signaling molecules that transmit signals from cell surface receptors directly to the nucleus. In the nucleus, they regulate transcription by interacting with both DNA elements and transcriptional coactivators and corepressors. Smads binds numerous transcriptional regulators like p53, CBP and the fos/jun family and are involved in cell-type specific gene expression.

Transcription factors Myogenic transcription factor MyoD is a putative regulator of the actions of myostatin. A family of transcription factors specifically expressed in the muscles, including myoD, myogenin, myf-5, and MRF-4/herculin/myf-6, have been cloned. These factors are phosphorylated nuclear proteins containing a helix-loop-helix (bHLH) motif, as required for both dimerization and DNA binding, and are believed to be determinants of the cell-specific differentiation program. When one of these factors is introduced into non-myogenic cells, differentiation into mature muscle cells is initiated. The myoD family, a group of transcription factors, has been found to direct muscle formation, inhibit proliferation, activate differentiation and induce a contractile phenotype. While myoD and myf-5 are expressed within the proliferating myoblasts, myogenin and MRF-4 are not expressed until the myoblasts withdraw from the cell cycle in response to mitogen withdrawal. Based on these findings, it was demonstrated that myogenin and MRF-4 activate and maintain the expression of muscle-specific genes, while myoD and myf-5 are thought to play a role in the proliferation of myoblasts.

The dystrophin gene The compositions and methods of the invention may include a gene modulator, e.g., an antisense oligonucleotide, that causes a change in the mutation seen in Duchenne muscular dystrophy (DMD) to a in-frame mutation. DMD, the most severe form of the disease, results from an abnormality in exon 19 of the dystrophin gene, which causes an out-of-frame shift of the amino acids reading frame of dystrophin mRNA. In contrast, in Becker muscular dystrophy (BMD), a much milder form of the disease, the reading frame is kept intact (i.e., in-frame) in spite of a partial deletion present in the gene and a dystrophin protein therefore is synthesized, though it differs in size from wild dystrophin. If the abnormal reading frame shift of DMD is converted to an in-frame arrangement, then DMD is converted to BMD, and amelioration of the symptoms would be expected. Exon 19 skipping can be artificially induced by administering to the patient an antisense oligonucleotide against exon 19, thus, the reading frame could turn in-frame again because of the total loss of 330 nucleotides from the pre-mRNA due to the loss of 242 nucleotides of exon 20 plus 88 nucleotides of exon 19.

It has been demonstrated that splicing out of exon 19 can be induced with an antisense oligonucleotide against exon 19 in the cells of a DMD patient having complete loss of exon 20 in mature dystrophin mRNA, and that the existing shift of the reading frame along the mature dystrophin mRNA can thereby be corrected, thus converting the dystrophin-negative cells to positive ones. Based on these results, antisense oligonucleotides targeted at parts of the dystrophin gene have been proposed as treatment of DMD. See, e.g., Japanese Laid-open Patent Application No. 11-140930, and U.S. Pat. Nos. 6,727,355; and 6,653,467 all of which are incorporated herein by reference. Accordingly, the compositions and methods of the invention may include a gene modulator, e.g., an antisense oligonucleotide, that causes a change in the mutation seen in DMD to a in-frame mutation.

Genes involved in cachexia Various pathways and modulators may be involved in cachexia. The fever-producing cytokines released by inflammatory cells and tumor cells are believed to contribute to cachexia. In fact, tumor necrosis factor (TNF), or cachectin, produces a laboratory model of cachexia when given to experimental, laboratory animals. Activins and myostatin are up-regulated in several types of cancer and infection, and could be therapeutic targets for cachexia. Myostatin has been shown to be involved in different types of cachexia. Myostatin administration in vivo induces severe weight loss and decreased muscle mass. In addition, accelerated proteolysis in muscle in fasting or denervation atrophy can be due to activation of the nonlysosomal (cytosolic) ATP-ubiquitin-dependent proteolyte process. The proteins involved in this process are potential targets for gene modulators. See, e.g., U.S. Pat. No. 5,972,636, which is incorporated herein by reference in its entirety. In fasting, the enhancement of muscle protein breakdown also requires glucocorticoids and low insulin and in febrile infections, requires interleukin-1 and TNF. A novel protein, cancer cachectic factor, also may be involved in the cachexia of, e.g., cancer, and presents another target for gene modulators as therapy. See, e.g., U.S. Pat. No. 5,834,192, which is incorporated herein by reference in its entirety.

Diabetes Since proper skeletal muscle function is important for normal glucose homeostasis, loss of activity of myostatin not only increases muscle mass but also prevents an age-related increase in the total mass of adipose tissues. Myostatin-deficient mice showed a reduction in fat accumulation with increasing age. The activin-follistatin system was also shown to be involved in development of the pancreas. It was suggested that follistatin's modulation of the formation of the exocrine pancreas was by inhibiting activin-like signaling molecules. Recently, using functional genomics tools, several secreted polypeptides with therapeutic applications in the treatment of diabetes, and BMP 9 were identified as potential inhibitors of glucose production and glycemia. Thus, in addition to adipocytokines such as leptin and adiponectin, multiple TGF-β family members including myostatin, activin and BMP 9 are involved in-glucose homeostasis and diabetes. Obese and insulin resistant mice with myostatin KO have less fat accumulation, low blood glucose and low insulin than their counterparts with wild-type myostatin, which led to the suggestion that inhibition of myostatin may be a treatment for type 2 diabetes mellitus.

In some embodiments, the invention provides methods of modulating the expression of one or more genes in cells by contacting cells with compositions of the invention. In these methods, cells to be treated contain a polynucleotide encoding a gene product that is involved in a muscle-wasting condition, or in muscle growth or muscle growth inhibition. Representative polynucleotides are shown in Tables 3, 4 and 5. The cell is contacted with any one of the compositions of oligonucleotides described herein for modulating expression of one or more polynucleotides. In some embodiments, the cell contains a polynucleotide encoding myostatin, myostatin transcription factor, myostatin activating protein, and/or myostatin receptor, and the composition with which the cell is contacted contains one or more oligonucleotides capable of modulating the expression of myostatin, myostatin transcription factor, myostatin activating protein, and/or myostatin receptor.

A method of the invention can be performed, for example, by contacting under suitable conditions a target cell and an oligonucleotide composition of the invention. Suitable conditions can be provided by placing the cell, which can be an isolated cell or can be a component of a tissue or organ, in an appropriate culture medium, or by contacting the cell in situ in an organism. For example, a medium containing the cell can be contacted with an oligonucleotide composition that, e.g., modulates expression of myostatin, myostatin signal transduction, myostatin receptors, myostatin transcription factors, myostatin-activating gene products, and the like. In general, the cell is a component of a tissue or organ in a subject, in which case contacting the cell can comprise administering the agent to the subject. However, the cell also can be manipulated in culture, then can be maintained in culture, administered to a subject, or used to produce a transgenic nonhuman animal. The level of mRNA expression of the target gene in the cell, tissue, organ, or animal, may be assessed using techniques that are known in the art, including, but are not limited to, Northern or Western blot analysis of tissue samples obtained from the cell, tissue, organ, or animal in situ hybridization analysis, and RT-PCR. Samples of cell, tissue, organ, or animal, may also be evaluated immunocytochemically using antibodies specific for the target gene product.

The present invention also provides methods, compositions, and kits for the treatment of animals. The term "animal" or "animal subject" as used herein includes humans as well as other mammals and non-mammals. The term "treating" and its grammatical equivalents as used herein include achieving a therapeutic benefit and/or a prophylactic benefit. By therapeutic benefit is meant eradication, amelioration, or prevention of the underlying disorder being treated. For example, in a diabetes patient, therapeutic benefit includes eradication or amelioration of the underlying diabetes, i.e., a return of blood sugar and blood insulin levels to normal or a trend toward normal. Also, a therapeutic benefit is achieved with the eradication, amelioration, or prevention of one or more of the physiological symptoms associated with the underlying disorder such that an improvement is observed in the patient, notwithstanding that the patient may still be afflicted with the underlying disorder. For example, administration of oligonucleotide compositions, described herein, to a patient suffering from muscular dystrophy, sarcopenia, spinal cord injury, neurodegenerative disease, anorexia, or cachexia, provides therapeutic benefit when an improvement is observed in the patient with respect muscular bulk, muscular strength, and the like. For prophylactic benefit, for example, the compositions of the invention may be administered to a patient at risk of developing a muscle wasting condition, for example, a patient undergoing prolonged bed rest,.or to a patient reporting one or more of the physiological symptoms of a muscle wasting disorder, or suffering from a conditions that predisposes the patient to a muscle wasting disorder, even though a diagnosis of a muscle wasting disorder may not have been made. For example, the oligonucleotide compositions of the invention may be administered to a patient with cancer where cachexia has not been diagnosed. In another example, compositions of the invention may be administered to a patient exhibiting Syndrome X who does not yet exhibit clinical symptoms of diabetes such as resting blood glucose elevated above the clinically accepted threshold value for diabetes. Thus, the method of treating of the present invention covers any treatment of symptoms of a disorder in an animal, preferably a mammal, particularly a human, and includes:

(a) preventing symptoms of a disorder from occurring in a subject that may be predisposed to a condition but has not yet been diagnosed as having it;
(b) inhibiting symptoms of a disorder (i.e., arresting its development); or
(c) relieving symptoms of a disorder (i.e., ameliorating and/or causing regression of-the condition); and/or
(d) maintaining homeostasis (i.e., the normal balance of RNA or DNA in a subject).

One of ordinary skill will appreciate that, from a medical practitioner's or patient's perspective, virtually any alleviation or prevention of an undesirable symptom would be desirable.

The dosages of the oligonucleotide composition in animals will depend on the disease or condition being, treated, the route of administration, and the physical characteristics of the animal being treated, and whether the treatment is nutritional, allopathic, or homeopathic.

The compositions of the present invention are formulated to contain a "nutritionally effective" or "allopathically effective" or "homeopathically effective" amount of one or more nucleic acid molecules. As used herein, the term "nutritionally effective" amount is meant to refer to an amount of a oligonucleotide composition that is non-toxic and greater than the minimum amount necessary to maintain a desired physiological effect. As used herein, the term "allopathically effective" amount is meant to refer to an amount of a oligonucleotide composition that is non-toxic and greater than the minimum amount necessary to produce a desired physiological effect. As used herein, the term "homeopathically effective" amount is meant to refer to an amount of a oligonucleotide composition that is non-toxic and is the lowest amount necessary to provide a desired physiological effect. A homeopathic effect, in accordance with the present invention, is achieved by a dose of modified nucleic acid that will be effective in treating (i.e., relieving, ameliorating, or preventing) symptoms of a particular condition or disease. Such treatment may be prophylactic in nature (i.e., completely or partially preventing the future occurrence of a symptom) and/or it may be therapeutic in nature (i.e., providing a partial or complete cessation or amelioration of a symptom).

Accordingly, in embodiments wherein the treatment utilizes allopathically effective amounts of compositions, the oligonucleotide compositions of the present invention may be administered at a unit dosage more than about 0.01, 0.05, 0.1, 0.5, 1, or 5 mg/kg, and/or less than about 10, 5, 1, 0.5, 0.1, or 0.05 mg/kg. Exemplary unit dosage ranges may be between about 0.01 mg/kg and 10 mg/kg, or between about 0.010 mg/kg and 1.0 mg/kg, or between about 0.10 mg/kg and 1.0 mg/kg for a composition that contains a single oligonucleotide. In some embodiments, the oligonucleotide compositions of the present invention are administered at unit dosages of about 0.01 to about 100 ug per kg of body weight, or about 0.1 to about 100 ug per kg of body weight, or about 0.1 to about 10 ug per kg of body weight, or about 1 to about 10 ug per kg of body weight, or about 1 to about 5 ug per kg of body weight. When more than one oligonucleotide is present in the composition, dosages of each oligonucleotide may be in the latter ranges, or dosage of one or more of the oligonucleotides may be decreased, based on the expected overall effect of the combination. In some embodiments, unit dosages per single oligonucleotide are at or below 100 ug per kg of body weight, or at or below 10 ug per kg of body weight, or at or below 1 ug per kg of body weight, or at or below 0.1 ug per kg of body weight, or at or below 0.01 ug per kg of body weight.

When orally administered, one dosage unit may be administered once every 10, 9, 8, 7, 6, 5, 4, 3, 2, or one day, or 1, 2, 3, 4, 5, 6, 7, 8, 9, 10, or more than 10 times per day until relief is achieved or until the symptoms disappear or are satisfactorily attenuated. In some embodiments, one dosage unit is administered about once to about four times per day. In some embodiments, a patient is instructed to orally take two to three dosage units per day. The dosage unit may be placed under the tongue of the patient or simply swallowed for such oral administration.

Modified oligonucleotides as described herein, e.g., achiral oligonucleotides of naturally occurring phosphodiester DNA and RNA linkages with 3' nuclease protection and sometimes also 5' nuclease protection, are not toxic, allowing a wide range of dosages to be possible with compositions of the present invention. For example, the dietary supplement recommendation for nucleic acids is 0.5 to 2.0 gm/day. Metabolites are naturally occurring compounds that occur in foods and as byproducts of cell catabolism. Furthermore, such compounds do not elicit an immune response. Accordingly, in some embodiments, dosages range from about 10 ug to 100 mg/kg/per day, or 0.01 gm to 10 gm/kg per day, or 0.01 to 1 gm/kg/day, or 0.01 to 0.1 gm/kg/day.

Homeopathic compositions typically employ substantially less nucleic acid than is employed in allopathic or nutritional compositions. Exemplary dosages to be employed in accordance with the present invention are described in Table 7. Furthermore, for homeopathic use, the oligonucleotide compositions of the present invention can be combined with any homeopathic drug and still elicit a therapeutic effect.

Oligonucleotide compositions of the present invention may be co-administered with other active pharmaceutical agents depending on the condition being treated. Pharmaceutical agents useful in the treatment of muscle wasting disorders, their optimal dosages and routes of administration, are known in the art. Co-administration can include simultaneous administration of the two agents in the same dosage form, simultaneous administration in separate dosage forms, and separate administration. In addition, oligonucleotide compositions of the present invention may be used in conjunction with other therapies, such as dietary therapy, dietary supplementation, physical therapy, exercise, and the like, which are used in the treatment of the disorders described herein.

The oligonucleotide composition can be administered by injection, topically, orally, transdermally, or rectally. Preferably, the composition is administered orally. The oral form in which the oligonucleotide is administered can include powder, tablet, capsule, solution, or emulsion. The effective amount can be administered in a single dose or in a series of doses separated by appropriate time intervals, such as hours.

In some embodiments, one or more of the oligonucleotides comprises at least one modification according to the present invention. A preferred modification is the incorporation of at least about three to eight contiguous achiral internucleoside phosphate linkages into the oligonucleotide backbone, or at least about nine to ten continuous achiral internucleoside phosphate linkages or at least about eleven to fifteen achiral internucleoside phosphate linkages, or the entire oligonucleotide contains achiral internucleoside phosphate linkages. In some embodiments the oligonucleotide is 3' end-blocked.

The methods of the present invention can be used to treat disorders including, but not limited to, muscular dystrophy, spinal cord injuries, neurodegenerative diseases, atrophy due to immobilization, bed rest, or weightlessness, sarcopenia, cachexia, and diabetes. Table 6 lists the target genes or combinations of target genes that are preferably employed in preparation of gene-modulating compositions of use in remedies for the treatment of various symptoms and conditions. In Table 6, the use a combination of target genes is denoted by a "/" (for example, "A/B/C" denotes the combination of target genes A, B and C); where two or more different combinations are preferred, each such combination is presented on a separate line. The gene-modulating compositions targeted at the genes are usually used in a 1:1:1 ratio, but this can vary. For example, in homeopathic treatments, a combination of 4×, 5×, and 6× solutions may be used, which deviates from 1:1:1. Any other ratio of compositions may also be used in combinations, depending on the condition to be treated, the state of the subject, and other factors that are known in the art.

Preferably, animals, e.g., mammals, are treated using compositions of the present invention having agents with compositions containing nucleic acid molecules having a sequence appropriate for the particular animal. Targeted species include, but are not limited to birds, fish, and mammals (especially chickens, pigs, goats, sheep, cows, dogs, horses, cats, and most preferably, humans). One of skill in the art can determine if a particular therapeutic course of treatment is successful by several methods known to those of skill in the art, including muscle fiber analysis or biopsy.

In a further aspect, the invention provides methods of increasing muscle mass of an animal where such an increase is desirable, e.g., in food or non-human sport animals, by administering to the animal an oligonucleotide composition of the invention, e.g., to modulate the expression of the myostatin gene. These methods produce animals having increased muscle and protein content, and, when the animals are used for food, also advantageously the muscles have reduced fat content. Oligonucleotide-based compositions as described herein that directly or indirectly regulate the expression of the myostatin region may be used to reduce expression of the myostatin gene product. Such oligonucleotide compositions may be administered to a livestock animal, including but not limited to cattle, sheep, pig, turkey, chicken, and fish, or to companion animals, particularly cats and dogs, to result in the decreased expression of myostatin in the animal and consequent higher than normal levels of muscle tissue, preferably without increased fat and/or cholesterol levels. A polynucleotide encoding a promyostatin or myostatin, or myostatin transcription factor, receptor, signal transduction factor, myostatin activating gene product can be derived from any organism where increased muscle mass may be desirable, preferably a food, sport or research animal, including, for example, mouse, rat, cow, pig, chicken, turkey, zebrafish, salmon, finfish, other aquatic organisms and other species. Examples of aquatic organisms include those belonging to the class Piscina, such as trout, char, ayu, carp, crucian carp, goldfish, roach, whitebait, eel, conger eel, sardine, flying fish, sea bass, sea bream, parrot bass, snapper, mackerel, horse mackerel, tuna, bonito, yellowtail, rockfish, fluke, sole, flounder, blowfish, filefish; those belonging to the class Cephalopoda, such as squid, cuttlefish, octopus; those belonging to the class Pelecypoda, such as clams (e.g., hardshell, Manila, Quahog, Surf, Soft-shell); cockles, mussels, periwinkles; scallops (e.g., sea, bay, calloo); conch, snails, sea cucumbers; ark shell; oysters (e.g., *C. virginica*, Gulf, New Zealand, Pacific); those belonging to the class Gastropoda such as turban shell, abalone (e.g. green, pink, red); and those belonging to the class Crustacea such as lobster, including but not limited to Spiny, Rock, and American; prawn; shrimp, including but not limited to *M. rosenbergii, P. styllrolls, P. indicus, P. jeponious, P. monodon, P. vannemel, M. ensis, S. melantho, N. norvegious*, cold water shrimp; crab, including, but not limited to, Blue, rook, stone, king, queen, snow, brown, dungeness, Jonah, Mangrove, soft-shelled; squilla, krill, langostinos; crayfish/crawfish, including, but not limited, to Blue, Marron, Red Claw, Red Swamp, Soft-shelled, white; Annelida; Chordata, including, but not limited to, reptiles such as alligators and turtles; Amphibia, including frogs; and Echinodermata, including, but not limited to, sea urchins.

Methods for increasing muscle mass in an animal where such increase is desirable are essentially the same as those used in treating disorders. Dosages, routes of administration, and durations of treatment may be adjusted as desired to produce the optimum development and timing of development, as appropriate for the use of the animal.

TABLE 1

Exemplary human target genes involved in muscle wasting conditions

| Genes | Accession Number |
|---|---|
| Myostatin | AF104922 |
| MyoD | NM002478 |
| ARIIb | NM001106 |
| TLL2 | AF059516 |
| ID-1 | NM002165 |
| TACE | NM003183 |
| TNF-R1 | NM001065 |
| IL6R | NM000565&NM181359 |
| MMP2 | NM004530 |
| FOXO1 | NM002015 |
| Bcl-3 | NM005178 |
| FOXO-3 | NM001455&NM201559 |
| E3alphaII | AY061884 |
| Nfkb-1 | NM003998 |
| IL1b | NM000576 |
| NF-IL6 | M83667 |
| NF-κB | M62399&L19067 |
| TNF-α | NM000594 |
| Caspase-3 | NM004346 |
| Caspase-1 | NM033292 |
| Atrogin-1 | NM058229&NM148177 |
| Smad-2 | AF027964 |
| PIF | AY90150 |
| IL-6 | NM000600 |

TABLE 2

Exemplary animal target genes involved in muscle growth and development

| Genes | Accession Number |
|---|---|
| Myostatin (Cow) | NM001001525 |
| Myostatin (Horse) | AB033541 |
| Myostatin (sheep) | AF019622 |
| Myostatin (goat) | AY436347 |
| Myostatin (Rabbit) | AY169410 |
| Myostatin (Pig) | NM214435&AF033855 |
| Myostatin (Chicken) | AF019621&AF346599 |
| Myostatin (Dog) | AY367768 |
| Myostatin (Fish) | AY825248 |
| Myostatin (Mouse) | NM01834 |
| TLII (mouse) | AF073526 |
| AcRIIB (mouse) | NM007397 |
| MyoD1 (mouse) | NM010866 |
| Atrogin-1 (mouse) | AF441120 |
| E3alpha-II (mouse) | XM358323 |

TABLE 2-continued

Exemplary animal target genes involved in muscle growth and development

| Genes | Accession Number |
|---|---|
| Foxo3 (mouse) | NM019740 |
| Foxo1 (mouse) | NM019739 |
| MuRF1 (mouse) | AF294790 |
| Caspase3 (mouse) | NM009810 |
| NFkB (mouse) | NM003998 |
| TNF-alpha (mouse) | NM013693 |
| TNF-R1 (mouse) | NM011609 |
| Caspase-1 (mouse) | BC008152 |
| TACE (mouse) | AB021709 |
| IL-1b (mouse) | NM008361 |
| IL-6 (mouse) | NM031168 |
| MMP2 (mouse) | NM008610 |
| p65 (mouse) | M61909 |
| IL-6R (mouse) | X53802 |
| Smad2 (mouse) | NM010754 |
| Cathepsin-B (mouse) | BC006656 |

TABLE 3

Antisense oligonucleotides targeted at human genes involved in muscle wasting

| Genes | Accession number | Antisense oligonucleotide sequences | Seq ID # |
|---|---|---|---|
| Myostatin | AF104922 | 5'-TgCCACACCAgTgAATCT-3' | 1 |
| | | 5'-gCAgTTTTTgCATgATTTTAA-3' | 2 |
| | | 5'-TAAATCTCATgAgCACCC-3' | 3 |
| MyoD | NM002478 | 5'-CAgAgAgTggCCggAACT-3' | 4 |
| | | 5'-TggCgCggCACggTCCTg-3' | 5 |
| | | 5'-AgTAgCTCCATATCCTgg-3' | 6 |
| | | 5'-AgAgCACCTggTATATCg-3' | 7 |
| ARIIb | NM001106 | 5'-CAgggCgCCgTCATgTTC-3' | 8 |
| | | 5'-gggTggCTCgTACgTgAC-3' | 9 |
| | | 5'-TgTCCTgggCTTAgATgC-3' | 10 |
| TLL2 | AF059516 | 5'-gCggCgCCCCCTgTCTTC-3' | 11 |
| | | 5'-AgggAgTTgCgTgCACgA-3' | 12 |
| | | 5'-ggCATggTggCgCggggC-3' | 13 |
| | | 5'-TCCCAgggCTgTgCAggA-3' | 14 |
| ID-1 | NM002165 | 5'-AgCCCgAAgCAgATACgg-3' | 15 |
| | | 5'-TCATgATTCTTggCgACT-3' | 16 |
| ID-1 | NM002165 | 5'-CATgATTCTTggCgACTg-3' | 17 |
| | | 5'-CCACTggCgACTTTCATg-3' | 18 |
| | | 5'-TCAgCgACACAAgATgCg-3' | 19 |
| | | 5'-CTTCAgCgACACAAgATg-3' | 20 |
| TACE | NM003183 | 5'-TTCTACCgCCAggCTCgA-3' | 21 |
| | | 5'-ACTgCCTCATgTTCCCgg-3' | 22 |

TABLE 3-continued

Antisense oligonucleotides targeted at human genes involved in muscle wasting

| Genes | Accession number | Antisense oligonucleotide sequences | Seq ID # |
|---|---|---|---|
| | | 5'-CCTCATgTTCCCggCCCC-3' | 23 |
| | | 5'-ACTAAATTAgCACTCTgT-3' | 24 |
| TNF-R1 | NM001065 | 5'-CAgTTgAgggTTgAgACT-3' | 25 |
| | | 5'-gCCCATgCCAgACAgCTA-3' | 26 |
| | | 5'-gCgCAgCCTCATCTgA-3' | 27 |
| IL6R | NM000565 & | 5'-TCCCTCTggCCCggCTCA-3' | 28 |
| | NM181359 | 5'-CCgACggCCAgCATgCTT-3' | 29 |
| | | 5'-CATTCTggggAAgAAgTA-3' | 30 |
| MMP2 | NM004530 | 5'-CAgCCTCCAgCCACCgCC-3' | 31 |
| | | 5'-gCCTCCATCgTAgCgCTC-3' | 32 |
| | | 5'-gCAgCCTAgCCAgTCggA-3' | 33 |
| FOXO1 | NM002015 | 5'-ggCCgCTTgCTCTCCCCA-3' | 34 |
| | | 5'-AgAggggggAgAACgCAgC-3' | 35 |
| | | 5'-CTCggCCATggTgACCCC-3' | 36 |
| | | 5'-ACCCTCAgCCTgACACCC-3' | 37 |
| Bcl-3 | NM005178 | 5'-gCggggCATCggggCATg-3' | 38 |
| | | 5'-gCCCCCCCATCCCCCTCA-3' | 39 |
| FOXO-3 | NM001455 & | 5'-ggggAgggACgTggACgC-3' | 40 |
| | NM201559 | 5'-CATCTTCgCCgCCCgC-3' | 41 |
| | | 5'-CCTTCAgCCTggCACCCA-3' | 42 |
| E3alphaII | AY061884 | 5'-CAATCAgTCCCggAgCCg-3' | 43 |
| | | 5'-TCCTCCCCAgCgCTACCg-3' | 44 |
| | | 5'-CTCTagCTCCgACgCCAT-3' | 45 |
| E3alphaII | AY061884 | 5'-TTggTggTgCAATAATTA-3' | 46 |
| Nfkb-1 | NM003998 | 5'-TCTCgCTCACTCTCTCAC-3' | 47 |
| | | 5'-gggAAgggCAggggAAgC-3' | 48 |
| | | 5'-gCgCgggCggAgggAAgC-3' | 49 |
| | | 5'-CTgCCATTCTgAAgCCgg-3' | 50 |
| | | 5'-gAAATTgTCAgCAggCTA-3' | 51 |
| IL1b | NM000576 | 5'-gAgAATCCCAgAgCAgCC-3' | 52 |
| | | 5'-CCATggCTgCTTCAgACA-3' | 53 |
| | | 5'-ggTACAgCTCTCTTTAgg-3' | 54 |
| NF-IL6 | M83667 | 5'-AgACgCggggCCgTCATgg-3' | 55 |
| | | 5'-gggAAgggCAggggAAgC-3' | 56 |
| | | 5'-CCTTTTCTAgCCCCgg-3' | 57 |

TABLE 3-continued

Antisense oligonucleotides targeted at human genes involved in muscle wasting

| Genes | Accession number | Antisense oligonucleotide sequences | Seq ID # |
|---|---|---|---|
| NF-κB | M62399 & L19067 | 5'-gAACAgTTCgTCCATg-3' | 58 |
| | | 5'-AgCCATTCGCCggAATTC-3' | 59 |
| | | 5'-gTgCACTACAgACgAgCC-3' | 60 |
| | | 5'-CTgCCATTCTgAAgCCgg-3' | 61 |
| | | 5'-ggCCCAgCTgCgACCCgg-3' | 62 |
| TNF-α | NM000594 | 5'-gggggTCTgTagTTgCTT-3' | 63 |
| | | 5'-CCAggggAgAgAgggTgg-3' | 64 |
| | | 5'-gCTCATggTgTCCTTTCC-3' | 65 |
| | | 5'-CATgCTTTCAgTgCTCAT-3' | 66 |
| | | 5'-gATgTTCgTCCTCCTCAC-3' | 67 |
| Caspase-3 | NM004346 | 5'-AggAgCCgCgTCTgCACT-3' | 68 |
| | | 5'-TTCTACAACCgCCTCACA-3' | 69 |
| | | 5'-TCTCCATggATACCTTTA-3' | 70 |
| | | 5'-ACCAACCATTTCTTTAgT-3' | 71 |
| Caspase-1 | NM033292 | 5'-ACCAACCATTTCTTTAgT-3' | 72 |
| | | 5'-TATTTTAATgTCCTgggA-3' | 73 |
| Atrogin-1 | NM058229 & NM148177 | 5'-ggATggggAgACggggCC-3' | 74 |
| Atrogin-1 | NM058229 & NM148177 | 5'-ggAATggCATggCACCgC-3' | 75 |
| | | 5'-TTCTACAACCgCCTCACA-3' | 76 |
| Smad-2 | AF027964 | 5'-TgTATCgAACCTCCCggC-3' | 77 |
| | | 5'-gACgACATgTTCTTACCA-3' | 78 |
| | | 5'-gCAAgATggACgACATgT-3' | 79 |
| | | 5'-TTTATgACATgCTTgTTgAgC-3' | 80 |
| | | 5'-TggTgAAgCTTTATgACA-3' | 81 |
| PIF | AY90150 | 5'-CTgTgTgCTggAgTgggT-3' | 82 |
| | | 5'-ATgAACCTCATgCTTCTg-3' | 83 |
| | | 5'-TCTCCTTACAgCTATAgT-3' | 84 |
| IL-6 | NM000600 | 5'-CTGTTTCgTTCCCggTgg-3' | 85 |
| | | 5'-AAGgAgTTCATAgCTggg-3' | 86 |
| | | 5'-CCATggTACATTTgCCgA-3' | 87 |

TABLE 4

Antisense oligonucleotide sequences targeted at animal genes involved in muscle growth and development

| Gene | Accession number | Antisense oligonucleotide sequences (5'-3') | SeqID# |
|---|---|---|---|
| Myostatin (chicken) | AF019621 & AF346599 | GAgATCCgggACAgCAAATgC | 88 |
| | | CCCCCTCTCCCTTTCCCCTTT | 89 |
| | | gCATTTTTTCTTACACCTCAC | 90 |
| | | CATAGACTGCTAgCTTTTgCA | 91 |
| | | CTgCCATCCAgAgCCACCggA | 92 |
| | | TCTgCTTCCACgTACAAgCAT | 93 |
| | | CTTgTTCCAggCgCAgTTTgC | 94 |
| | | TgCAgTggAggAgCTTTgggT | 95 |
| | | TCgTCTTCCAAAgAgCCATCg | 96 |
| | | CagACTCCgTaggCATTgTgA | 97 |
| Myostatin (chicken) | AF019621 & AF346599 | TagACTAAACTTAAAgAAgC | 98 |
| | | CCgTTgTaggTTTTTggACTT | 99 |
| | | TCTgCCAgATAGCAgTgCCTg | 100 |
| | | TgTTTgAgCCAATTTTgCAgC | 101 |
| | | gCAAgATCTCgTCCAgTCTCA | 102 |
| | | gTgTCTgTAACTCTgACCTCT | 103 |
| | | CgggTAgCgACAACATCgggA | 104 |
| | | gTgCTATAATCCAgTCCCATC | 105 |
| | | AATTCgCATTCTCCggAgCAg | 106 |
| | | gCCTgCTgAgCCTCTgggATT | 107 |
| | | TACAgCATgTTTATAggggAC | 108 |
| | | ACgATCTACAACCATggCTgg | 109 |
| | | TCATgAgCACCCgCAACgATC | 110 |
| | | TCTCACgTCAgCCAAAATTCA | 111 |
| Myostatin (pig) | NM214435 & AF033855 | TgCCTgCACTgTCTgAgAgAC | 112 |
| | | TgCTTTTgAgTAACgCCAAgC | 113 |
| | | CATgATTTTAAAATCAATACA | 114 |
| | | TgCAgTTTTTgCATgATTTTA | 115 |
| | | CATAgATTTgCAgTTTTTgCA | 116 |
| | | TCAgATCCACgggACCAgCAA | 117 |
| | | ACATgCATTACACAgCCCCTC | 118 |
| | | TCCAggCgAAgTTTACTgAgg | 119 |
| | | gATCAATCAgTTCCCgAgTG | 120 |
| | | TTCcAAggAgCCATCACTgCT | 121 |
| | | AgAAgATCAgACTCTgTAggC | 122 |
| | | TAAAgAAgCAgCATTTgggTT | 123 |
| | | TCTTGACgggTCTCAgATATA | 124 |

TABLE 4-continued

Antisense oligonucleotide sequences targeted at animal genes involved in muscle growth and development

| Gene | Accession number | Antisense oligonucleotide sequences (5'-3') | SeqID# |
|---|---|---|---|
| | | TgggTTTgATgAgTCTCAggA | 125 |
| | | CagTgCCTgggTTCATgTCAA | 126 |
| Myostatin (pig) | NM214435 & AF033855 | TgAgCCAATTTTgCAACACTg | 127 |
| | | TgACCATTCTCATgTAAAgCT | 128 |
| | | ggATTCAgCCCATCTTCTCCT | 129 |
| | | gAgTgCTCATCACAgTCgAgT | 130 |
| | | TgCAATAATCCAgTCCCATCC | 131 |
| | | ACAAgATgAgTgTgAgggTAT | 132 |
| | | TgTgggAgTACAgCAggggCC | 133 |
| | | ACCATggCTggAATTTTCCCA | 134 |
| | | AATCTCATgAgCACCCACAgC | 135 |
| Myostatin (cow) | NM001525 | gAgTAAcGcCAAgCCAAACgT | 136 |
| | | TCCCTTgTTCTTACTTCTTCC | 137 |
| | | gCAgTTTTTgCATggTTTTAA | 138 |
| | | CCTTCTgCTCgCTgTTCTCAT | 139 |
| | | gTTTTCCCTCCACAAACATgC | 140 |
| | | TTTgCTgATgTTAggAgCTgT | 141 |
| | | gCTggCATCTCTCTggACATC | 142 |
| | | AtgACCgTTTCCgTCCTggCg | 143 |
| | | gTTTTCCTTCCACTTgCgTTA | 144 |
| | | CACAgTTgggCCTTTACTAgT | 145 |
| | | ACACTgTCgCAggAgTCTTgA | 146 |
| | | TCCAgTATACCTTgTACCgTC | 147 |
| | | TCTgCCAAATACCAgTgCCTg | 148 |
| | | AgATCATggCCATTCTCATCT | 149 |
| | | TCCATCTTCTCCTggTTCTgg | 150 |
| | | CCTAgATcTTTTTggTgTgTC | 151 |
| | | TagAgggTAACgACAgCATCg | 152 |
| | | TCTCCAGAGCAgTAATTggCC | 153 |
| | | AggAgTACAgCAggggCCggC | 154 |
| | | TCATgAACACCCACAgCgATC | 155 |
| Myostatin (horse) | AB033541 | TgAgTAACgCCAAgCCAA | 156 |
| | | CAgTTTTTgCATggTTTT | 157 |
| | | TCATgAACACCCACAgCg | 158 |

TABLE 4-continued

Antisense oligonucleotide sequences targeted at animal genes involved in muscle growth and development

| Gene | Accession number | Antisense oligonucleotide sequences (5'-3') | SeqID# |
|---|---|---|---|
| Myostatin (sheep) | AF019622 | TgAgTAACgCCAAgCCAA | 159 |
| | | CAgTTTTTgCATggTTTT | 160 |
| | | TCATgAACACCCACAgCg | 161 |
| Myostatin (goat) | AY436347 | TgAgTAACgCCAAgCCAA | 162 |
| | | CAgTTTTTgCATggTTTT | 163 |
| | | TCATgAACACCCACAgCg | 164 |

TABLE 5

Antisense oligonucleotides equences targeted at human myostatin gene

| Antisense oligonucleotide sequences (5'-3')* | SequenceID# |
|---|---|
| ACTTgCCACACCAgTgAATCT | 165 |
| TCTTgTTCTTgTTTCTTCCTT | 166 |
| gTTgCAgTTTTTgCATgATTT | 167 |
| ACACAgAgTTgCAgTTTTTgC | 168 |
| AATCAgCATAAACAggTAAAT | 169 |
| AgATCCACTggACCAgCAACA | 170 |
| ACACAgCCCCTCTTTTTCCAC | 171 |
| gAgCTgTTTCCAgACgAAgTT | 172 |
| AgTggAggAgCTTTgggTAAA | 173 |
| TCgCTgCTgTCATCCCTCTgg | 174 |
| CCgTTgTagCgTgATAATCgT | 175 |
| AGAAAATCAgACTCTgTAggC | 176 |
| CATAgTTgggCCTTTACTACT | 177 |
| TTgTAggAgTCTCgACgggTC | 178 |
| CATAggTTTgATgAgTCTCAg | 179 |
| AgTgCCTgggTTCATgTCAAg | 180 |
| TCTTCACATCAATgCTCTgCC | 181 |
| ATgCCTAAgTTggATTCAggT | 182 |
| gCCCATCTTCTCCTggTCCTg | 183 |
| gTgTgTCTgTTACCTTgACCT | 184 |
| TgTTgAgTgCTCATCACAgTC | 185 |
| ATCCAATCCCATCCAAAAgCT | 186 |
| TCCAgAgCAgTAATTggCCTT | 187 |
| gTgTACCAgATgAgTATgAgg | 188 |

TABLE 5-continued

Antisense oligonucleotides equences targeted at human myostatin gene

| Antisense oligonucleotide sequences (5'-3')* | SequenceID# |
|---|---|
| TgggAgTACAgCAAgggCCTg | 189 |
| TCgCTggAATTTTCCCATATA | 190 |
| ATATAAATCTCATgAgCACCC | 191 |

*Based on AF104922.

TABLE 6

Exemplary combinations
of oligonucleotides for treatment of muscle wasting
Combinations of oligonucleotides targeting the following genes Myo
Myo/myoD
Myo/ActRIIB
Myo/myoD/ActRIIB
Myo/ActRIIB/Smad2
Myo/NF-kB
Myo/Atrogin-1
Myo/MuRF1
Myo/Atrogin-1/MuRF1
Atrogin-1/FOXO1
Atrogin-1/FOXO3
Atrogin-1/FOXO1/FOXO3
Myo/MyoD/ActIIB/Samd2/NF-kB
Atrogin-1/FOXO1/FOXO3/MuRF1

TABLE 7

| Homeopathic RNA/DNA Dosages | |
|---|---|
| Dilution/Potency | µg/kg |
| 2x | 50 |
| 3x | 5 |
| 4x | 0.5 |
| 5x | 0.05 |
| 6x | 0.005 |

III. Kits

In still another aspect, the present invention provides kits for the treatment of muscle wasting conditions and/or for the improvement of muscle growth and maintenance. These kits comprise a composition containing a gene-modulating oligonucleotide as described herein and instructions teaching the use of the kit according to the various methods and approaches described herein. Such kits may also include information, such as scientific literature references, package insert materials, clinical trial results, and/or summaries of these and the like, which indicate or establish the activities and/or advantages of the composition. Such information may be based on the results of various studies, for example, studies using experimental animals involving in vivo models and studies based on human clinical trials. Kits described herein can be provided, marketed and/or promoted to health providers, including physicians, nurses, pharmacists, naturopaths, homeopaths, chiropractors, formulary officials, and the like. Kits for nutritional or homeopathic use may be provided, marketed and/or promoted directly to consumers.

EXAMPLES

Example 1

Determination of Combined Effect of Myostatin RNA Oligonucleotides in Cell Culture System Cell Growth and Culture C2C12 is a mouse myoblast cell line (ATCC CRL-1772), which differentiates rapidly, forming contractile myotubes and producing characteristic muscle proteins. The cells were maintained in Dulbecco's Modified Eagle Medium (DMEM) (Gibco-BRL) supplemented with 10% FCS, 1% L-glutamine, 0.5% penicillin and 0.5% streptomycin. They were incubated at 37° C. under 5% $CO_2$ in a moist atmosphere. Cells approaching 50-70% confluency were washed in phosphate buffered saline (PBS) and detached with 0.25% (w/v) Trypsin—0.53 mM EDTA solution. The detached cells were resuspended in serum-supplemented media and centrifuged at 1000 rpm at room temperature for 5 minutes. The supernatant was discarded and the cells were subcultured at a diluted cell concentration.

Transfection

The RNA oligonucleotides were tested in cells singly and in combinations. The uptake of RNA oligonucleotides into cells was enhanced by complexing with Lipofectamine 2000. Approximately $1 \times 10^5$ C2C12 cells were seeded in 0.5 ml of growth medium without antibiotics in 24-well dishes 1 day before transfection. Cells reached approximately 50% confluency after being incubated at 37° C. overnight.

For each transfection sample, dilute the appropriate amount of RNA was diluted oligonucleotides in 50 µl of Opti-MEM® I Reduced Serum Medium without serum. Then one µl of Lipofectamine 2000 in 50 µl of Opti-MEM® I Medium was added. Mixed gently and incubated for 5 minutes at room temperature. After the 5-minute incubation, combined the diluted RNA oligonucleotides with the diluted Lipofectamine. 2000 (total volume is 100 µl). The sample was then mixed gently and incubated for 20 minutes at room temperature to allow the RNA oligonucleotide:Lipofectamine. 2000 complexes to form.

100 µl of siRNA:Lipofectamine. 2000 complexes was added to each well (2 µM of final concentration of RNA oligonucleotides). The cells were incubated at 37° C. in a $CO_2$ incubator for 24-72 hours until they were ready to assay for gene knockdown.

Protein Analysis

The cellular protein of treated and untreated C2C12 cells was extracted for immunoblot analysis. The cells were harvested and placed on ice before being resuspended in RIPA buffer (100 mM Tris-Cl, 300 mM NaCl, 0.1% SDS, 2% NP-40, 1% sodium deoxychoate) with freshly added 100 µg/ml PMSF and 1 µg/ml aprotinin. The cell extracts were then sheared by passing through a 22-gauge needle 13 times and an extra 1 µl of PMSF was added. After standing on ice for 30-60 minutes, the cell lysate was centrifuged at 10,000×g for 10 minutes at 4° C. The protein-containing supernatant was collected and its concentration estimated using the Biorad protein assay system (Biorad Laboratories, Richmond, Calif.).

Protein analysis was accomplished by immunoblots also known as Western blots. Approximately 40 µg of each sample was run on a 10% SDS-PAGE gel (Invitrogen). Gel was then electrotransferred onto nitro-cellulose membrane in cold transfer buffer at 30V for an hour. The membrane was blocked with 3% BSA in TBS-T (10 mM Tris-Cl, 150 mM NaCl, 0.1% Tween-20) for 30 minutes. The membrane was then treated with Blotto A (5% skim milk powder in TBS-T) with the appropriate primary antibody (anti-myostatin and anti-MyoD) for an hour at room temperature followed by washing with TBS-T. The membrane was then probed with horseradish peroxidase conjugated secondary antibody for 45 minutes at room temperature and then washed as described above. The immunocomplexes were detected by chemiluminescence reaction using reagents provided in the Amersham RCL kit (Amersham) and then exposed onto Hyperfilm (Amersham). The film was then developed to reveal protein bands.

To ensure even loading, β-actin primary antibody was used to immunoblot the membrane as a control. A densitometry was performed to quantitate the intensities of each band produced from Western analysis.

Results

The results showed that C2C12 cells could be efficiently transfected with RNA oligos at a efficiency of over 50%. When seven RNA oligos were screened in the cells, all showed activity at inhibition of the myostatin expression with three being most active: A (ATg Tag CgT CCg AgA gAC (SEQ ID NO: 193), targeted at the 5'UTR), B (TgC ATC ATT TTA AAA ATC AgC (SEQ ID NO: 194), targeted at the translation start site) and C (ACC TAA TgC AAA gCT CAT (SEQ ID NO: 195), targeted at the translation stop region), as assayed by western blots. All three RNA oligos are modified with 2'-Omethyl and 3'-butanol blocked.

Example 2

Effect of Single and Combined RNA Oligos on the Muscle Weight in Mice

This Example was designed to test the effect of antisense oligonucleotides directed to myostatin genes.

Materials Oligonucleotides: 3 oligonucleotides (A, B, C as in the Example 1) were straight 2'-methoxy.

Sample preparation: Each oligo was dissolved in saline. For the A+B+C Group, 3 RNA oligos were mixed in equal volume. 100 ul of each mixture was used to inject mice at a dose of 5 mg/kg.

Experimental procedure Female mice (6-8 weeks) were housed for 7 days before injections started (Day 1). Mice were divided into five groups randomly: Group A (RNA oligo A), Group B (RNA oligo B) and Group C (RNA oligo C), Group D (RNA oligos A+B+C mixture) and Group D (saline). In each cycle of the treatment, tail vein IV injection was performed at day 1, IP injection followed at day 2 and 3. Ten treatment cycles were planned in the protocol. During the experiment, the protocol was adjusted after the cycle 5 with only IV injections performed. Each day, body weight was measured before injections. At the end of the experiment, a portion of the quadriceps (rectus femoris) were dissected and weighed. Samples were divided for pathology (fixed) and molecular analysis (liquid nitrogen).

Results

Bodyweight All mice were measured for their body weight each day, and all mice grew normally with a consistent increase of body weight.

Effect of oligos on muscle weight The muscle weight was measured for each group. As shown in the following table 8, compared with the saline control group, the all RNA oligo-treated group showed a increase in the muscle weight (P<0.05), with the combined oligos being the most effective

TABLE 8

Comparison of single and combined effect on muscle weight

|  | A | B | C | A + B + C |
|---|---|---|---|---|
| Increase in muscle weight(%) | 0.8 | 2.4 | 7.2 | 8.8 |

This example demonstrates that treatment with modified RNA antisense oligonucleotides of the invention promotes muscle growth.

Example 3

Specificity of the Effect of RNA Oligo on the Muscle Weight in Mice

This Example was designed to test the effect of the combined antisense oligonucleotides directed to myostatin gene on muscle weight and the target gene expression.

Materials Oligonucleotides: 3 oligonucleotides (A, B, C as in the Example 1) were straight 2'-methoxy.

Sample preparation: 3 RNA oligos were mixed in equal volume. 100 ul of each mixture was used to inject mice at a dose of 5 mg/kg.

Experimental procedure Female mice (6-8 weeks) were housed for 7 days before injections started (Day 1). Mice were divided into three groups randomly: Group A (RNA oligos A+B+C), Group B (three control DNA oligos) and Group C (saline). In each cycle of the treatment, tail vein IV injection was performed at day 1, IP injection followed at day 2 and 3. Ten treatment cycles were planned in the protocol. During the experiment, the protocol was adjusted after the cycle 5 with only IV injections performed. Each day, body weight was measured before injections. At the end of the experiment, a portion of the quadriceps (rectus femoris) were dissected and weighed. Samples were divided for pathology (fixed) and molecular analysis (liquid nitrogen).

Results

Bodyweight All mice were measured for their body weight each day, and all mice grew normally with a consistent increase of body weight.

Effect of oligos on muscle weight The muscle weight was measured for each group. As shown in the following table 9, compared with the saline and DNA oligo control groups, the combined RNA oligo-treated group showed a increase in the muscle weight (P<0.05).

TABLE 9

Specific Effect of the combined RNA oligos on muscle weight

|  | Combined RNA | Control oligos |
|---|---|---|
| Increase in muscle weight (%) | 11.3 | −0.4 |

When the muscle tissues were collected and assayed for the expression of the myostatin gene by Western blots, it was shown that the combined RNA oligos could significantly inhibit the myostatin expression, while no effect was observed for the house-keeping gene β-actin.

This example demonstrates that treatment with modified RNA antisense oligonucleotides of the invention could specifically inhibit the target gene expression, leading to the increase in the muscle weight.

Example 4

Delivery of RNA Oligos via Different Routes

This Example was designed to test the effect of the combined antisense oligonucleotides directed to myostatin gene on muscle weight by three different delivery routes.

Materials Oligonucleotides: 3 oligonucleotides (A, B, C as in the Example 1) were straight 2'-methoxy.

Sample preparation: 3 RNA oligos were mixed in equal volume. 100 ul of each mixture was used to inject mice at a dose of 5 mg/kg.

Experimental procedure Female mice (6-8 weeks) were housed for 7 days before injections started (Day 1). Mice were divided into four groups randomly: Group A (iv injection, every three days), Group B (iv and ip injection at every other days), Group C (saline, delivered as in Group B) and Group D (oral). At the end of the experiment, a portion of the quadriceps (rectus femoris) were dissected and weighed. Samples were divided for pathology (fixed) and molecular analysis (liquid nitrogen).

Results

Bodyweight All mice were measured for their body weight each day, and all mice grew normally with a consistent increase of body weight.

Effect of oligos on muscle weight The muscle weight was measured for each group. As shown in the following table 10, compared with the saline control group, all three delivery routes showed a increase in the muscle weight (P<0.05).

TABLE 10

Effect of combined RNA oligos on muscle weight in three different delivery route

|  | iv | iv + ip | Oral |
|---|---|---|---|
| Increase in muscle weight (%) | 25.91 | 22.38 | 18.55 |

This example demonstrates that treatment with modified RNA antisense oligonucleotides of the invention could promote the muscle growth via different delivery routes.

Example 5

Inhibition of Foxo1 Leads to Increase in Muscle Weight in Both Normal and Cancer-bearing Mice Experimental Procedures Animal, Oligonucleotides and Delivery Methods—BALB/c female mice (6-8 weeks old) weighing 15 to 18 g were used for normal and cancer model. Sarcoma S-180 cells in 0.2 ml of PBS ($5 \times 10^6$ cell) were i.p. injected and grown for 7-10 days. Six mice per group were treated with RNA oligos via tail vein injection (100 ug/0.1 ml) every two days. Mice were weighed everyday during the treatment period. Oligoribonucleotides targeted to Foxo1 and a control oligo were used in the experiment. Mice were sacrificed at desired time points, and muscles were weighed and snap-frozen in liquid nitrogen and stored at −80° C.

RNA Extraction and Real-time PCR analysis—Total RNA was extracted in TRIzol (Invitrogen). RNA was separated electrophoretically on agarose gels under denaturing conditions in order to confirm the integrity of ribosomal RNA bands. Single-strand cDNA synthesis was carried out from 2 ug of total RNA by the reverse transcription (RT) reaction (Promega). Real-time fluorescence quantitative PCR was performed by using an Applied Biosystems Prism 7000 instrument, an Applied Biosystems SYBR® green master mix reagent and oligonucleotide pairs to the endogenous control gene Beta-actin, MyoD, GDF-8 and foxo-1 cDNA. The reagents were denatured at 95° C. for 10 mins, followed by 40 cycles of 15 s at 95° C. and 60 s at 60° C. 5' to 3' primer sequences were as follows:

```
                                    (SEQ ID NO: 196)
Beta-actin     GAA CCC TAA GGC CAA CCG TGA A
forward (SEQ ID NO: 197)
Beta-actin     CTC AGT AAC AGT CCG CCT AGA A
reverse, (SEQ ID NO: 198)
MyoD forward   5'GCA AGA CCA CCA ACG CTG AT 3'

(SEQ ID NO: 199)
MyoD reverse   5'GGT TCG GGT TGC TGG ACG TG 3'

(SEQ ID NO: 200)
GDF-8 forward  5'CAG ACC CGT CAA GAC TCC TAC A 3'

(SEQ ID NO: 201)
GDF-8 reverse  5'CAG TGC CTG GGC TCA TGT CAA G 3'

(SEQ ID NO: 202)
FOXO 1 forward 5'GTA CGC CGA CCT CAT CAC CA 3'

(SEQ ID NO: 203)
FOXO 1 reverse 5'TGC TGT CGC CCT TAT CCT TG 3'
```

Average $C_T$ values for MyoD, GDF-8 and foxo1 were calculated and normalized to $C_T$ values for Beta-actin. And the normalized values were subjected to a $2^{-\Delta\Delta Ct}$ formula to calculate the fold change between the control and experiment groups. The formula and its derivations were obtained from the ABI Prism 7000 Sequence Detection System user guide. All reactions were performed in duplicates or triplicates.

Western blotting—Protein was extracted from the muscle tissue of different groups with lysis buffer containing 100 mM Tris-HCl, 0.05% CA-630, 100 ug/ml PMSF, 100 ug/ml DTT, 1 ug/ml Aprotinin and 1 ug/ml Lenpeptin. Protein concentration of each specimen was detected by the Bradford method (Bio-Rad Laboratories). The samples were heat denatured at 95° C. for 5 min, electrophoretically separated on a 12.5% SDS-PAGE, and transferred to a PVDF membrane. The membrane was blocked with 5% non-fat dry milk in TBST buffer(50 mM Tris-HCl, 100 mM NaCl, and 0.1% Tween-20, pH 7.4) and incubated with monoclonal anti-MyoD diluted at 1/200 (BD, Pharmingen), monoclonal anti-Myostatin diluted at 1/100(Santa Cruz Biotechnology) and anti-beta actin diluted at 1/250(Santa Cruz Biotechnology), and further incubated for 90 min at 37° C.Bound antibodies were visualized by subsequent chemiluminescent reaction with a horseradish peroxidase conjugated IgG(1:3000) in the ECL system (Amersham).

The image and data were analyzed with bandscan 5.0 software.

Statistical analysis—Data were expressed as means±SD and subjected to one-way AVONA with factors of treatment, genotype or wild type. Comparisons between two groups were performed by unpaired Student's t test. A value of p<0.05 was considered significantly different.

Results

Foxo 1 RNA oligonucleotide promoted muscle growth in normal mice

Figure 2:
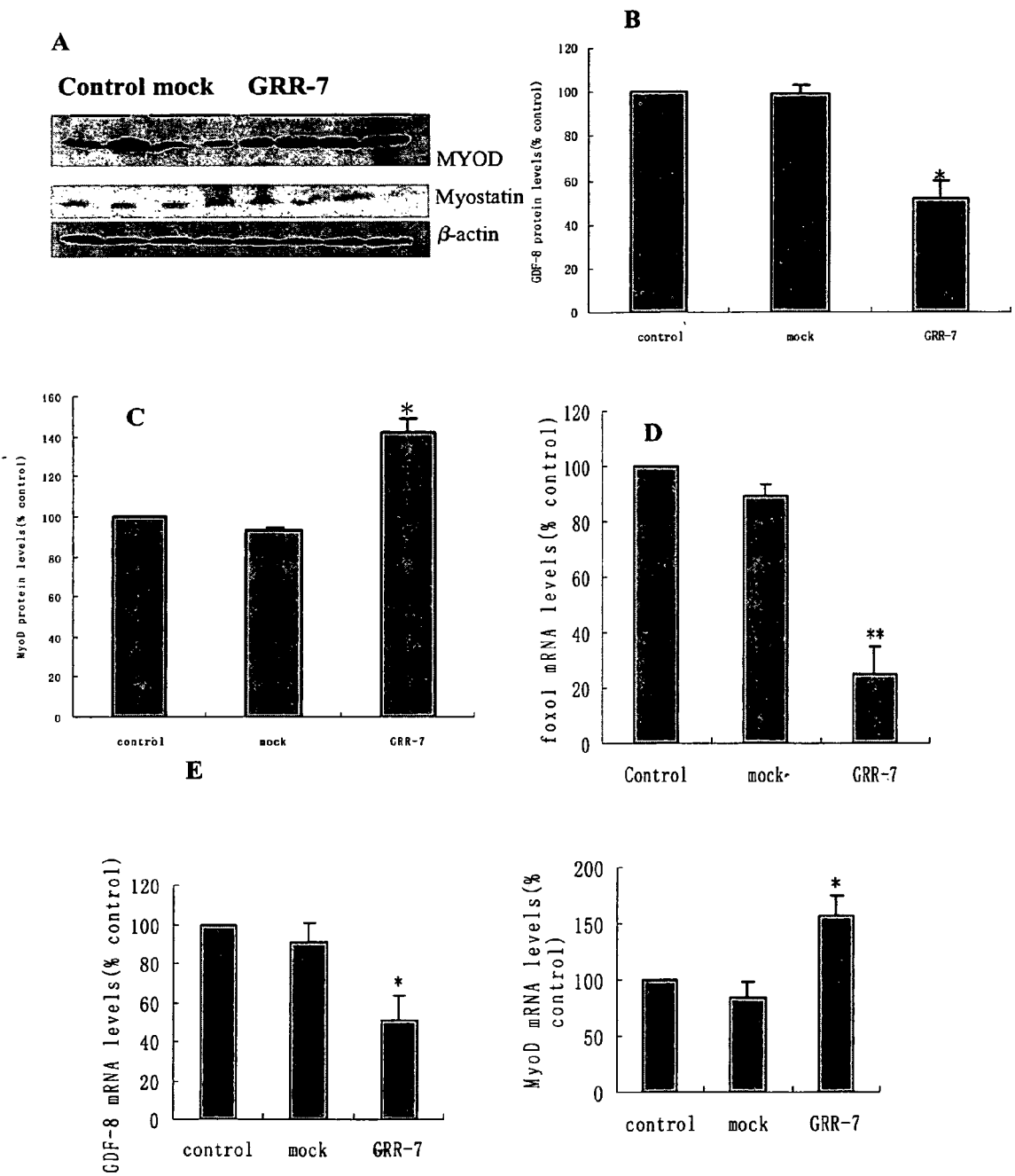
FIG. 2 depicts the effect of RNA oligos targeted to Foxo1 on expression of MyoD and GDF-8 in normal mice. A, Western blots were performed on the effect of RNA oligo on protein expression level of MyoD (C) and GDF-8 (B) in normal mice. Quantitative RT-PCR analysis was done on the effect of RNA oligo on mRNA expression level of Foxo1 (D), GDF-8 (E) and MyoD (F) in normal mice. Data are mean±SD (n=6), $P<0.01$*.

In order to examine the effects of the Foxo1 RNA oligo on the muscle growth, the leg muscles were collected and weighed at the end of the treatment. The results showed that the mass of muscles of normal mice was increased by 10% while no significant change was observed in the control groups (FIG. 1). When the muscle tissues were analyzed for the expression of the target gene, it was shown that the protein levels of GDF-8 decreased by 48.5% and the MyoD increased by 42% compared to control group (FIG. 2). At the RNA level as measured by Real Time PCR, the mRNA levels of Foxo1 decreased by 75%, GDF-8 decreased by 49% MyoD increased by 58% compared to control group (FIG. 2). This result clearly demonstrated that the Foxo1 RNA oligo could increase the muscle growth by direct inhibition of the Foxo1 expression and indirect impact on the myostatin and MyoD expression.

2. Increase Muscle Weight in Cancer Cachexia Model by Foxo1 RNA Oligonucleotide

Figure 3:
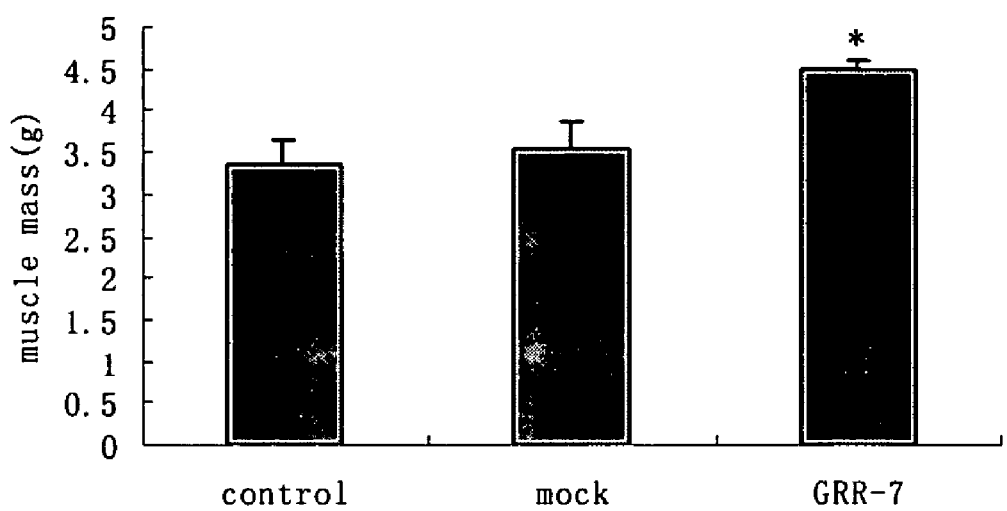
FIG. 3 depicts the effect of RNA oligos targeted to Foxo1 (GRR-7) and control on mass of muscles in S-180 tumor mice. Dissected muscle mass at the end of the study (n=6), $P<0.01$*.
Figure 4:
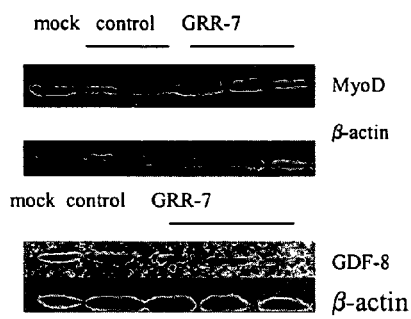
FIG. 4 depicts the effect of RNA oligos targeted to Foxo1 on expression of MyoD and GDF-8 in S180 mice. A, Western blots were performed on the effect of RNA oligo on protein expression level of GDF-8 (B) and MyoD (C) in S180 mice. Quantitative RT-PCR analysis was done on the effect of RNA oligo on mRNA expression level of Foxo1 (D), GDF-8 (E) and MyoD (F) in normal mice. Data are mean±SD (n=6), $P<0.01$**.
Figure 4:
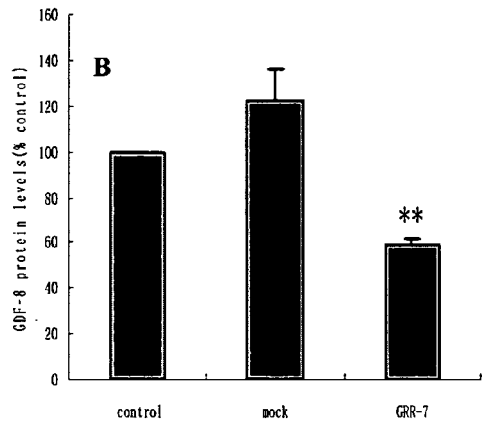
Figure 4:
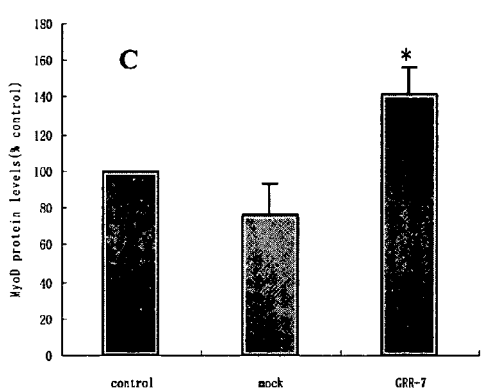
Figure 4:
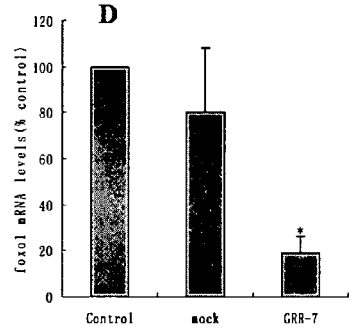
Figure 4:
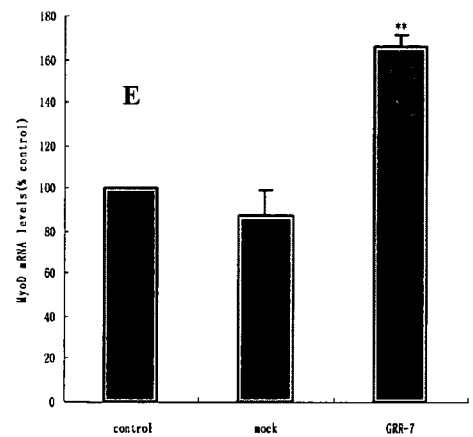
Figure 4:
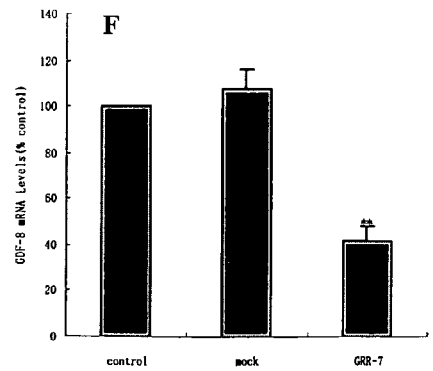

To test the RNA oligo effect on muscle mass in a relevant disease model, an ascetic tumor S180 was used as a cancer cachexia model where the muscle loss is a characteristic. As for in the normal mice, the group injected with Foxo1 RNA oligo showed a muscle mass increased by 32.8% compared to control group (FIG. 3). At protein level, myostatin decreased by 40.4%, MyoD increased by 41.8% (FIG. 4). At mRNA level, foxo1 expression decreased by 81%, myostatin decreased by 58%, MyoD increased by 66% compared to control group (FIG. 4). This result demonstrated that the use of Foxo1 oligo could impact on the muscle growth in cancer cachexia model.

Example 6

Inhibition of Myostatin Gene Expression by RNA Oligos Increased Muscle Growth in Tumor-bearing Mice Experimental Procedures Animal, Oligonucleotides and Delivery Methods— BALB/c female mice (6-8 weeks old) weighing 15 to 18 g were used for cancer model. Sarcoma S-180 cells in 0.2 ml of PBS ($5 \times 10^6$ cell) were i.p. injected and grown for 7-10 days. Six mice per group were treated with RNA oligos via tail vein injection (100 ug/0.1 ml) every two days. Mice were weighed everyday during the treatment period. Oligonucleotides targeted to Myostatin and a control oligo were used in the experiment. Mice were scarified at desired time points, and leg muscles including the quadriceps (rectus femoris), the gastrocnemius, triceps, and the EDL were weighed and snap-frozen in liquid nitrogen and stored at $-80°$ C.

Statistical analysis—Data were expressed as means±SD and subjected to one-way AVONA with factors of treatment, genotype or wild type. Comparisons between two groups were performed by unpaired Student's t test. A value of $p<0.05$ was considered significantly different.

Quantitative RT-PCR analysis of mRNA—Total RNA was isolated from cells using RNA preparation kits from TRI-ZOL® reagent (Invitrogen). cDNA was generated using ImpromII® reverse transcriptase (Promega) and oligo(d)T primers, according to the manufactures instructions, typically using 1 μg of total RNA per reaction. Quantitative PCR was performed using an Applied Biosystems Prism 7000 instrument using Applied Biosystems SYBR® green master mix reagent and oligonucleotide pairs to human cell house-keeping gene beta-actin cDNA. 5' to 3' primer sequences were as follows: Beta-actin forward GAA CCC TAA GGC CAA CCG TGA A (SEQ ID NO: 196), Beta—actin reverse, CTC AGT AAC AGT CCG CCT AGA A (SEQ ID NO: 197), GDF-8 forward CAG ACC CGT CAA GAC TCC TAC A (SEQ ID NO: 200), GDF-8 reverse CAG TGC CTG GGC TCA TGT CAA G (SEQ ID NO: 201), MyoD forward GCA AGA CCA CCA ACG CTG AT (SEQ ID NO: 198), MyoD reverse GGT TCG GGT TGC TGG ACG TG (SEQ ID NO: 199). Average $C_T$ values for MyoD and GDF-8 were calculated and normalized to $C_T$ values for Beta-actin. The average Ct value from each three experiments was calculated, and the results were graphed with the corresponding standard deviation indicated with error bars in the figures. The formula and its derivations were obtained from the ABI Prism 7000 Sequence Detection System user guide.

Statistical analysis—Data were expressed as means±SD and subjected to one-way AVONA with factors of treatment, genotype or wild type. Comparisons between two groups were performed by unpaired Student's t test. A value of $p<0.05$ was considered significantly different.

Results

Figure 5:
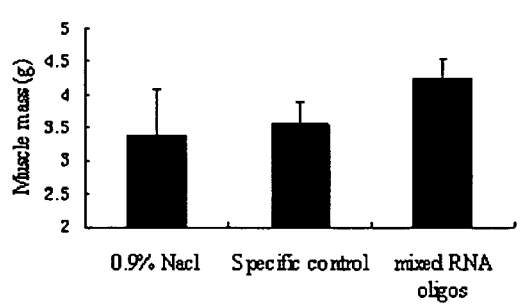
FIG. 5 depicts the effect of RNA oligos targeted to myostatin on muscle mass in S-180 implanted mice: (A) Dissected muscle mass at the end of the study. Results showed that muscle mass was increased by 26% in mixed RNA oligos compared to control group (n=6, mean±SD, $p<0.05$)0.5 (B) The ratio of muscle leg's mass to body. The results indicated that mixed RNA oligos targeted to myostatin could increase muscle mass in S-180 tumor mice (mean±SD, $p<0.05$). 5 (C and D) Quantitative RT-PCR analysis of myostatin and MyoD expression at mRNA level in mouse model after injecting RNA oligos 2 weeks ($P<0.01$).
Figure 5:
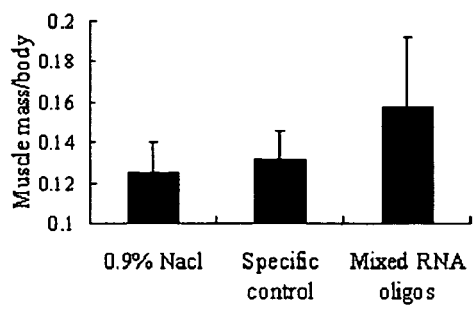
Figure 5:
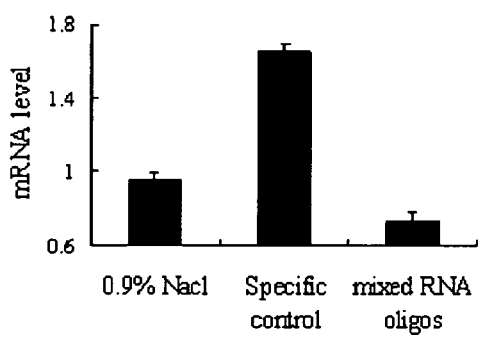
Figure 5:
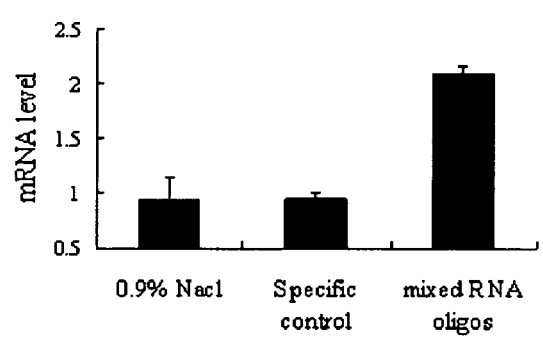

RNA oligos targeted to myostatin gene decreased myostatin expression and increased the mass of muscles in S-180 implanted mice The three RNA oligos targeted at the Myostatin gene were mixed in an equal mole and the mixture was used in the experiment. The effect on muscle mass in S-180 implanted mice was tested in S-180 implanted mice. The results showed that the muscle mass in the group treated with the RNA oligo mixture increased by 26% compared to control group (FIG. 5A, $p<0.05$). As in FIG. 5B, the ratio of skeletal muscle mass and body mass in the group injected RNA oligos increased by 10.4% ($p<0.05$). At mRNA level, myostatin decreased by 21.3% (FIG. 5C, $p<0.01$), MyoD increased by 1.23-fold compared to control group (FIG. 5D, $p<0.01$).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating a muscle wasting condition comprising administering to an individual suffering from a muscle wasting condition an effective amount of a composition suitable for administration to an animal comprising
   a modified oligonucleotide containing 7 to 75 contiguous ribose groups linked by achiral 5' to 3' internucleoside phosphate linkages,
   wherein the modified oligonucleotide is complementary to a region of a gene selected from the group consisting of the 5' UTR region, translational start site, the 3' UTR, and translational termination site, and
   wherein the gene encodes FOXO1.

2. A method of promoting muscle growth in an individual comprising administering to the individual an effective amount of a composition suitable for administration to an animal comprising
   a modified oligonucleotide containing 7 to 75 contiguous ribose groups linked by achiral 5' to 3' internucleoside phosphate linkages,
   wherein the modified oligonucleotide is complementary to a region of a gene selected from the group consisting of the 5' UTR region, translational start site, the 3' UTR, and translational termination site, and
   wherein the gene encodes FOXO1.

3. The method of claim 1 or 2 wherein the individual is a mammal.

4. The method of claim 1 or 2 wherein the individual is a human.

5. The method of claim 1, wherein the modified oligonucleotide comprises one or more nucleotides in which the 2' position comprises a substituent.

6. The method of claim 5, wherein the 2' substituent is selected from the group consisting of hydrogen, methoxy, propoxy, methoxy-ethoxy, fluorine, chlorine, bromine and iodine.

7. The method of claim 1, wherein the modified oligonucleotide is 3' and/or 5' end-modified.

8. The method of claim 1, wherein the modified oligonucleotide is 3' and/or 5' end-blocked.

9. The method of claim 1, wherein the modified oligonucleotide is an antisense oligonucleotide.

10. The method of claims 1, further comprising a plurality of modified oligonucleotides containing 7 to 75 contiguous ribose groups linked by achiral 5' to 3' internucleoside phosphate linkages, wherein the plurality of modified oligonucleotides are complementary to regions of a gene selected from the group consisting of the 5' UTR region, translational start site, the 3' UTR, and translational termination site, and wherein said gene codes for a gene product involved in a muscle wasting condition.

11. The method of claim 1, further comprising two modified oligonucleotides containing 7 to 75 contiguous ribose groups linked by achiral 5' to 3' internucleoside phosphate linkages, wherein said modified oligonucleotides are complementary to regions of a gene selected from the group consisting of the 5' UTR region, translational start site, the 3' UTR, and translational termination site, and wherein said gene codes for a gene product involved in a muscle wasting condition.

12. The method of claim 1, wherein said oligonucleotide comprises one or more nucleotides in which the 2' position comprises a substituent, and wherein the modified oligonucleotide is 3' and/or 5' end-blocked.

13. The method of claim 2, wherein said oligonucleotide comprises one or more nucleotides in which the 2' position comprises a substituent, and wherein the modified oligonucleotide is 3' and 5' end-blocked.

* * * * *

SEQUENCE LISTING

<160> NUMBER OF SEQ ID NOS: 203

<210> SEQ ID NO 1
<211> LENGTH: 18
<212> TYPE: DNA
<213> ORGANISM: Artificial Sequence -continued

```
<220> FEATURE:
<223> OTHER INFORMATION: Description of Artificial Sequence: Synthetic
      oligonucleotide

<400> SEQUENCE: 1
tgccacacca gtgaatct                                                    18

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gcagtttttg catgatttta a                                                21

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
taaatctcat gagcaccc                                                    18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cagagagtgg ccggaact                                                    18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tggcgcggca cggtcctg                                                    18

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
agtagctcca tatcctgg                                                    18

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
```

```
                              oligonucleotide

<400> SEQUENCE: 7
agagcacctg gtatatcg                                                       18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
cagggcgccg tcatgttc                                                       18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gggtggctcg tacgtgac                                                       18

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tgtcctgggc ttagatgc                                                       18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gcggcgcccc ctgtcttc                                                       18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
agggagttgc gtgcacga                                                       18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 13
ggcatggtgg cgcggggc                                                   18

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tcccagggct gtgcagga                                                   18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agcccgaagc agatacgg                                                   18

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tcatgattct tggcgact                                                   18

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
catgattctt ggcgactg                                                   18

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ccactggcga ctttcatg                                                   18

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
```
tcagcgacac aagatgcg                                                    18

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cttcagcgac acaagatg                                                    18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ttctaccgcc aggctcga                                                    18

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
actgcctcat gttcccgg                                                    18

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cctcatgttc ccggcccc                                                    18

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
actaaattag cactctgt                                                    18

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cagttgaggg ttgagact                                                    18

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gcccatgcca gacagcta                                                 18

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gcgcagcctc atctga                                                   16

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tccctctggc ccggctca                                                 18

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
ccgacggcca gcatgctt                                                 18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cattctgggg aagaagta                                                 18

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cagcctccag ccaccgcc                                                 18

<210> SEQ ID NO 32

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gcctccatcg tagcgctc                                                  18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gcagcctagc cagtcgga                                                  18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ggccgcttgc tctcccca                                                  18

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35 agaggggggag aacgcagc                                                 18

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ctcggccatg gtgacccc                                                  18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
accctcagcc tgacaccc                                                  18

<210> SEQ ID NO 38
<211> LENGTH: 18
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 38
gcggggcatc ggggcatg                                               18

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gcccccccat ccccctca                                               18

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
ggggagggac gtggacgc                                               18

<210> SEQ ID NO 41
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
catcttcgcc gcccgc                                                 16

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ccttcagcct ggcaccca                                               18

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
caatcagtcc cggagccg                                               18

<210> SEQ ID NO 44
<211> LENGTH: 18
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 44
tcctccccag cgctaccg                                                   18

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ctctagctcc gacgccat                                                   18

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ttggtggtgc aataatta                                                   18

<210> SEQ ID NO 47
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
tctcgctcac tctctcac                                                   18

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gggaagggca ggggaagc                                                   18

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gcgcgggcgg agggaagc                                                   18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 50
ctgccattct gaagccgg                                          18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gaaattgtca gcaggcta                                          18

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
gagaatccca gagcagcc                                          18

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
ccatggctgc ttcagaca                                          18

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ggtacagctc tctttagg                                          18

<210> SEQ ID NO 55
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
agagcgcggc cgtcatgg                                          18

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56

```
gggaagggca ggggaagc                                              18
```

<210> SEQ ID NO 57
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57

```
cctttctag ccccgg                                                 16
```

<210> SEQ ID NO 58
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58

```
gaacagttcg tccatg                                                16
```

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59

```
agccattcgc cggaattc                                              18
```

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60

```
gtgcactaca gacgagcc                                              18
```

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61

```
ctgccattct gaagccgg                                              18
```

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62

```
ggcccagctg cgacccgg                                              18
```

```
<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gggggtctgt agttgctt                                                 18

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
ccaggggaga gagggtgg                                                 18

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
gctcatggtg tcctttcc                                                 18

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
catgctttca gtgctcat                                                 18

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gatgttcgtc ctcctcac                                                 18

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
aggagccgcg tctgcact                                                 18
```

```
<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ttctacaacc gcctcaca                                                  18

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
tctccatgga tacctttta                                                 18

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
accaaccatt tctttagt                                                  18

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
accaaccatt tctttagt                                                  18

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
tattttaatg tcctggga                                                  18

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
ggatggggag acggggcc                                                  18

<210> SEQ ID NO 75
<211> LENGTH: 18
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
ggaatggcat ggcaccgc                                                  18

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
ttctacaacc gcctcaca                                                  18

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
tgtatcgaac ctcccggc                                                  18

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
gacgacatgt tcttacca                                                  18

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
gcaagatgga cgacatgt                                                  18

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tttatgacat gcttgttgag c                                              21

<210> SEQ ID NO 81
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 81
tggtgaagct ttatgaca                                                  18

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
ctgtgtgctg gagtgggt                                                  18

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
atgaacctca tgcttctg                                                  18

<210> SEQ ID NO 84
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
tctccttaca gctatagt                                                  18

<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
ctctttcgtt cccggtgg                                                  18

<210> SEQ ID NO 86
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
aaggagttca tagctggg                                                  18

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 87
ccatgctaca tttgccga                                              18

<210> SEQ ID NO 88
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
cagatccggg acagcaaatg c                                          21

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 89 cccctctcc ctttccccctt t                                          21

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90 gcatttttc ttacacctca c                                           21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
catagactgc tagcttttgc a                                          21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
ctgccatcca gagccaccgg a                                          21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 93
tctgcttcca cgtacaagca t                                              21

<210> SEQ ID NO 94
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
cttgttccag gcgcagtttg c                                              21

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
tgcagtggag gagctttggg t                                              21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
tcgtcttcca aagagccatc g                                              21

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97
cagactccgt aggcattgtg a                                              21

<210> SEQ ID NO 98
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 98
tagagctaaa cttaaagaag c                                              21

<210> SEQ ID NO 99
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
```

```
ccgttgtagg tttttggact t                                               21

<210> SEQ ID NO 100
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tctgccagat accagtgcct g                                               21

<210> SEQ ID NO 101
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
tgtttgagcc aattttgcag c                                               21

<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
gcaagatctc gtccagtctc a                                               21

<210> SEQ ID NO 103
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gtgtctgtaa ctctgacctc t                                               21

<210> SEQ ID NO 104
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
cgggtagcga caacatcggg a                                               21

<210> SEQ ID NO 105
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gtgctataat ccagtcccat c                                               21
```

<210> SEQ ID NO 106
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
aattcgcatt ctccggagca g                                              21

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gcctgctgag cctctgggat t                                              21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
tacagcatgt ttatagggga c                                              21

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
acgatctaca accatggctg g                                              21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
tcatgagcac ccgcaacgat c                                              21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tctcacgtca gccaaaattc a                                              21

<210> SEQ ID NO 112

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
tgcctgcact gtctgagaga c                                              21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
tgcttttgag taacgccaag c                                              21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
catgatttta aaatcaatac a                                              21

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
tgcagttttt gcatgatttt a                                              21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
catagatttg cagtttttgc a                                              21

<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
tcagatccac gggaccagca a                                              21

<210> SEQ ID NO 118
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 118
acatgcatta cacagcccct c                                             21

<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
tccaggcgaa gtttactgag g                                             21

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
gatcaatcag ttcccggagt g                                             21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
ttccaaggag ccatcactgc t                                             21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
agaagatcag actctgtagg c                                             21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
taaagaagca gcatttgggt t                                             21

<210> SEQ ID NO 124
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 124
tcttgacggg tctcagatat a                                              21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
tgggtttgat gagtctcagg a                                              21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
cagtgcctgg gttcatgtca a                                              21

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
tgagccaatt ttgcaacact g                                              21

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
tgaccattct catctaaagc t                                              21

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
ggattcagcc catcttctcc t                                              21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 130
gagtgctcat cacagtcgag t                                          21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
tgcaataatc cagtcccatc c                                          21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
acaagatgag tgtgagggta t                                          21

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
tgtgggagta cagcaggggc c                                          21

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
accatggctg gaattttccc a                                          21

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
aatctcatga gcacccacag c                                          21

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
```
gagtaacgcc aagccaaacg t                                              21

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
tcccttgttc ttacttcttc c                                              21

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138 gcagttttttg catggtttta a                                             21

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
ccttctgctc gctgttctca t                                              21

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
gttttccctc cacaaacatg c                                              21

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
tttgctgatg ttaggagctg t                                              21

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
gctggcatct ctctggacat c                                              21

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
atgaccgttt ccgtcctggc g                                           21

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144
gttttccttc cacttgcgtt a                                           21

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145
cacagttggg cctttactag t                                           21

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146
acactgtcgc aggagtcttg a                                           21

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
tccagtatac cttgtaccgt c                                           21

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 148
tctgccaaat accagtgcct g                                           21

```
<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
agatcatggc cattctcatc t                                              21

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 150
tccatcttct cctggttctg g                                              21

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
cctagatctt tttggtgtgt c                                              21

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 152
tagagggtaa cgacagcatc g                                              21

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 153
tctccagagc agtaattggc c                                              21

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 154
aggagtacag cagggccgg c                                               21

<210> SEQ ID NO 155
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
tcatgaacac ccacagcgat c                                            21

<210> SEQ ID NO 156
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
tgagtaacgc caagccaa                                                18

<210> SEQ ID NO 157
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157 cagttttgc atggtttt                                                 18

<210> SEQ ID NO 158
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
tcatgaacac ccacagcg                                                18

<210> SEQ ID NO 159
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
tgagtaacgc caagccaa                                                18

<210> SEQ ID NO 160
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160 cagttttgc atggtttt                                                 18

<210> SEQ ID NO 161
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 161
tcatgaacac ccacagcg                                                 18

<210> SEQ ID NO 162
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
tgagtaacgc caagccaa                                                 18

<210> SEQ ID NO 163
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
cagtttttgc atggtttt                                                 18

<210> SEQ ID NO 164
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 164
tcatgaacac ccacagcg                                                 18

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 165
acttgccaca ccagtgaatc t                                             21

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
tcttgttctt gtttcttcct t                                             21

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 167
gttgcagttt ttgcatgatt t                                              21

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
acacagagtt gcagtttttg c                                              21

<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
aatcagcata aacaggtaaa t                                              21

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
agatccactg gaccagcaac a                                              21

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 171
acacagcccc tcttttcca c                                               21

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
gagctgtttc cagacgaagt t                                              21

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide -continued

<400> SEQUENCE: 173
agtggaggag ctttgggtaa a                                              21

<210> SEQ ID NO 174
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
tcgctgctgt catccctctg g                                              21

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
ccgttgtagc gtgataatcg t                                              21

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
agaaaatcag actctgtagg c                                              21

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
catagttggg cctttactac t                                              21

<210> SEQ ID NO 178
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
ttgtaggagt ctcgacgggt c                                              21

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179

```
cataggtttg atgagtctca g                                              21

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
agtgcctggg ttcatgtcaa g                                              21

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
tcttcacatc aatgctctgc c                                              21

<210> SEQ ID NO 182
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
atgcctaagt tggattcagg t                                              21

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
gcccatcttc tcctggtcct g                                              21

<210> SEQ ID NO 184
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
gtgtgtctgt taccttgacc t                                              21

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
tgttgagtgc tcatcacagt c                                              21
```

```
<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
atccaatccc atccaaaagc t                                                  21

<210> SEQ ID NO 187
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
tccagagcag taattggcct t                                                  21

<210> SEQ ID NO 188
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
gtgtaccaga tgagtatgag g                                                  21

<210> SEQ ID NO 189
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
tgggagtaca gcaagggcct g                                                  21

<210> SEQ ID NO 190
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
tcgctggaat tttcccatat a                                                  21

<210> SEQ ID NO 191
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
atataaatct catgagcacc c                                                  21

<210> SEQ ID NO 192
```

```
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
ggctagctac aacga                                                        15

<210> SEQ ID NO 193
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
atgtagcgtc cgagagac                                                     18

<210> SEQ ID NO 194
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
tgcatcattt taaaaatcag c                                                 21

<210> SEQ ID NO 195
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
acctaatgca aagctcat                                                     18

<210> SEQ ID NO 196
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 196
gaaccctaag gccaaccgtg aa                                                22

<210> SEQ ID NO 197
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 197
ctcagtaaca gtccgcctag aa                                                22

<210> SEQ ID NO 198
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 198
gcaagaccac caacgctgat                                                  20

<210> SEQ ID NO 199
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 199
ggttcgggtt gctggacgtg                                                  20

<210> SEQ ID NO 200
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 200
cagacccgtc aagactccta ca                                               22

<210> SEQ ID NO 201
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 201
cagtgcctgg gctcatgtca ag                                               22

<210> SEQ ID NO 202
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 202
gtacgccgac ctcatcacca                                                  20

<210> SEQ ID NO 203
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 203
tgctgtcgcc cttatccttg                                                  20
```